US008609387B2

(12) United States Patent
Valtakari et al.

(10) Patent No.: US 8,609,387 B2
(45) Date of Patent: Dec. 17, 2013

(54) FUNGAL ENDOGLUCANASES, THEIR PRODUCTION AND USE

(75) Inventors: Leena Valtakari, Rajamäki (FI); Marika Alapuranen, Rajamäki (FI); George Szakacs, Budapest (HU); Jarno Kallio, Järvenpää (FI); Pentti Ojapalo, Tuusula (FI); Jari Vehmaanperä, Klaukkala (FI); Terhi Puranen, Nurmijärvi (FI)

(73) Assignee: AB Enzymes Oy, Rajamaki (FI)

( * ) Notice: Subject to any disclaimer, the term of this patent is extended or adjusted under 35 U.S.C. 154(b) by 162 days.

(21) Appl. No.: 13/142,609

(22) PCT Filed: Dec. 28, 2009

(86) PCT No.: PCT/FI2009/051043
§ 371 (c)(1),
(2), (4) Date: Jun. 29, 2011

(87) PCT Pub. No.: WO2010/076388
PCT Pub. Date: Jul. 8, 2010

(65) Prior Publication Data
US 2011/0269212 A1 Nov. 3, 2011

(30) Foreign Application Priority Data
Dec. 30, 2008 (FI) ...................................... 20086253

(51) Int. Cl.
| | |
|---|---|
| C12N 15/00 | (2006.01) |
| C12N 1/20 | (2006.01) |
| C12N 9/42 | (2006.01) |
| C07K 1/00 | (2006.01) |
| C07H 21/04 | (2006.01) |

(52) U.S. Cl.
USPC ..................... 435/209; 435/320.1; 435/252.3; 536/23.1; 530/350

(58) Field of Classification Search
USPC ..................... 435/183, 252.3, 320.1; 530/350
See application file for complete search history.

(56) References Cited

U.S. PATENT DOCUMENTS

| | | | |
|---|---|---|---|
| 5,792,641 | A | 8/1998 | Schülein et al. |
| 7,256,032 | B2 | 8/2007 | Valtakari et al. |
| 2008/0145912 | A1 | 6/2008 | Schülein et al. |

FOREIGN PATENT DOCUMENTS

| | | |
|---|---|---|
| EP | 0244234 A2 | 4/1987 |
| EP | 1123974 A1 | 8/2001 |
| EP | 1700917 A1 | 9/2006 |
| WO | 95/33386 A1 | 12/1995 |
| WO | 97/08325 A2 | 3/1997 |
| WO | 2007/071818 A1 | 6/2007 |
| WO | 2007/071820 A1 | 6/2007 |

OTHER PUBLICATIONS

International Search Report Relating to corresponding PCT/FI2009/051043, 2011.
Altschul, et al., "Basic Local Alignment Search Tool," J. Mol. Biol. (1990) 215, 403-410.
Bailey, et al., "Induction, Isolation and Testing of Stable *Trichoderma reesei* Mutants With Improved Production of Solubilizing Cellulase," Enzyme Microb. Technol., 1981, vol. 3, April.
Bendtsen, et al., "Improved Prediction of Signal Peptides: SignalP 3.0," J. Mol. Biol. (2004) 340, 783-795.
Chao, et al., "Aligning Two Sequences Within a Specified Diagonal Band," CABIOS, vol. 8, No. 5, 1992, 481-487.
Haakana, et al., "Cloning of Cellulase Genes from *Melanocarpus albomyces* and Their Efficient Expression in *Trichoderma reesei*," Enzyme and Microbial Technology 34 (2004) 159-167.
Henrissat, "A Classification of Glycosyl Hydrolases Based on Amino Acid Sequence Similarities," Biochem. J. (1991) 280, 309-316.
Henrissat, et al., "New Families in the Classification of Glycosyl Hydrolases Based on Amino Acid Sequence Similarities," Biochem J. (1993) 293, 781-788.
Henrissat, et al., "Updating the Sequence-Based Classification of Glycosyl Hydrolases," Biochem J. (1996) 316, 695-696.
Hirschberg, et al., "A Linear Space Algorithm for Computing Maximal Common Subsequences," Communications of the ACM, Jun. 1975, vol. 18, No. 6.
Joutsjoki, et al., "Transformation of the *Trichoderma reesei* with the *Hormoconis resinae* Glucoamylase P (gamP) Gene: Production of a Heterologous glucoamylase by *Trichoderma reesei*," Curr Genet (1993) 24:223-228.
Karhunen, et al., "High Frequency One-Step Gene Replacement in *Trichoderma reesei*. I. Endoglucanase I Overproduction," Mol Gen Genet (1993) 241:515-522.
Malardier, et al., "Cloning of the Nitrate Reductase Gene (niaD) of Aspergillus Hidulans and its Use for Transformation of Fusarium Oxysporum," Gene. 78 (1989) 147-156.
Murashima, et al., "Exploring Amino Acids Responsible for the Temperature Profile of Glycoside Hydrolase Family 45 Endoglucanase EGL3 from *Humicola grisea*," Biosci. Biotechnol. Biochem., 70 (9), 2205-2212, 2006.
Myers, et al., "Optimal Alignments in Linear Space," CABIOS, vol. 4. No. 1, Nov. 17, 1988.
Needleman, et al., "A General Method applicable to the Search for Similarities in the Amino Acid Sequence of Two Proteins," J. Mol. Biol. (1970) 48, 443-453.
Nielsen, et al., "Identification of Prokaryotic and Eukaryotic Signal Peptides and Prediction of their Cleavage Sites," Protein Engineering vol. 20, No. 1, 1-6, 1997.
Nierstrasz, et al., "Process Engineering and Industrial Enzyme Applications," Textile Processing With Enzymes, 4.1, 120, 2003.

(Continued)

*Primary Examiner* — Maryam Monshipouri
(74) *Attorney, Agent, or Firm* — Banner & Witcoff, Ltd.

(57) ABSTRACT

Novel fungal endoglucanases with substantial performance at low temperatures are disclosed. The endoglucanases are conveniently produced by recombinant technology, and means for their production are described. The endoglucanases are used for treating cellulosic material, especially in textile industry, e.g. in biofinishing or biostoning. They may also be used in detergents, in animal feed and/or in pulp and paper industry or bioethanol production.

21 Claims, 5 Drawing Sheets

(56) References Cited

OTHER PUBLICATIONS

Paloheimo, et al., "High-Yield Production of a Bacterial Xylanase in the Filamentous Fungus *Trichoderma reesei* Requires a Carrier Polypeptide With an Intact Domain Structure," Applied and Environmental Microbiology, Dec. 2003, vol. 69, No. 12, 7073-7082.

Penttila, et al., "A Versatile Transformation System for the Cellulolytic Filamentous Fungus *Trichoderma reesei*," Gene, 61 (1987) 155-164.

Rice, et al., "EMBOSS: The European Molecular Biology Open Software Suite," TIG, Jun. 2000, vol. 16, No. 6.

Shimonaka, et al., "Molecular Cloning of a Gene Encoding Endo-β-D-1,4-Glucanase PCE1 from Phycomyces Nitens," Biosci. Biotechnol. Biochem., 68 (11), 2299-2305, 2005.

van Zyl, et al., "Consolidated Bioprocessing for Bioethanol Production Using *Saccharomyces cerevisiae*," Adv Biochem Engin/Biotechnol (2007) 108: 205-235.

Office Action issued from corresponding European Patent Application No. 09836130.6, dated Nov. 8, 2012.

Baba, Yuko, et al., "Alternative Splicing Produces Two Endoglucanases with One or Two Carbohydrate-Binding Modules in Mucor circinelloides," Journal of Bacteriology, May 2005, pp. 3045-3051, vol. 187, No. 9, American Society for Microbiology.

Shimonaka, Atsushi, et al., "Specific Characteristics of Family 45 Endoglucanases from Mucorales in the Use of Textiles and Laundry," Bioscience Biotechnolohy and Biochemistry, Apr. 2006, pp. 1013-1016, vol. 70, No. 4.

Database Uniprot, "SubName: Full=Glycoside hydrolase 45, ID Q69F59_GIBZE," Nov. 25, 2008.

A)

B)

A

B

C

D

E

SEQUENCE LISTING

```
<160> NUMBER OF SEQ ID NOS: 23

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
taytgggayt gytgyaarcc                                                 20

<210> SEQ ID NO 2
<211> LENGTH: 17
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t

<400> SEQUENCE: 2
tggtgytgyg cntgyta                                                    17

<210> SEQ ID NO 3
<211> LENGTH: 17
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t

<400> SEQUENCE: 3
tarcangcrc arcacca                                                    17

<210> SEQ ID NO 4
```

```
<211> LENGTH: 17
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t

<400> SEQUENCE: 4
gtrcanccrt craadat                                                    17

<210> SEQ ID NO 5
<211> LENGTH: 23
<212> TYPE: DNA
<213> ORGANISM: Artificial sequence
<220> FEATURE:
<223> OTHER INFORMATION: primer

<400> SEQUENCE: 5
ttrtcsgcrt tytgraacca rtc                                             23

<210> SEQ ID NO 6
<211> LENGTH: 648
<212> TYPE: DNA
<213> ORGANISM: Geomyces pannorum

<400> SEQUENCE: 6
tactgggact gctgcaaacc ctcctgcgcc tggtcaggca aggcctcatt caaaaccggt      60
cccgtgcagt cctgtgacaa gggcgacaat gtgctcgcag acgcagacac caagtccgca    120
tgcgacaacg gtggcccagc ctttatgtgc tccgatgaga gcccatgggc cgtctcagac    180
agcctggcct atggattcgc tgcggtgtcc atatcgggtg gcactgaggc gagctggtgc    240
tgtgcttgct acgagttgac gttcacgagc ggcccagtgt caggcaagaa gatggtcgtg    300
caggcgacaa atacgggtgg tgaccttggc cagaatcact ttgatatcgg cgtacgtata    360
ccgtttctgt cctcgtcttt cttctttcta ccccctcgacg tcccttcaca tcccctctcc    420
atcagctcct acacctcatt tatataagaa tccctcaact aaccaccacc agatgcccgg    480
cggcggcttc ggcctcttca acgcctgcac tccccaatac ggcacgcctt ccaccggctg    540
gggaaatcaa tacggcggcc tcacctcgcg gagccaatgc gacgccttcc cccaggccct    600
caaagccggt tgctactgga ggttcgactg gttccaaaac gccgcaca                 648

<210> SEQ ID NO 7
<211> LENGTH: 588
<212> TYPE: DNA
<213> ORGANISM: Geomyces pannorum

<400> SEQUENCE: 7
tattgggatt gttgtaagcc gtcctgcggc tgggccgaca agcagactt cgtcgacaag       60
tctccagtcc aatcatgcga tatcaacgca atccgctgc tggatgttac tcaggggacc     120
ggttgcaatg gcggcaatgc gttcggatgt gcgtcgaact cgccgtgggc cgtcaatgac    180
acgttctcct acggcttcgt gggcactttc ctcattggcg gcgacgagtc cagctggtgc    240
tgcagctgct tccaattgaa ctttaccagc ggggcagtca aaggcaaatc gatgattgtg    300
caggcctcca acacgaatta cgattctcca gacgcgaatg tcttcactct tggtgtatgt    360
actccttttcc ccgcagattg ggagttacgc ccgtactaat gccttctatc agatacctgg    420
tggaaataca agctatgctg gcgcttgtgc tatcgaatac aacgtctcag attctgtgtt    480
```

```
cggcacggaa aacgtgggcg tatctaatcg caccgactgt gatgaccttc ccgcagcact    540
gaagcctggt tgccagtggc ggttcgactg gttccagaat gcggataa                 588

<210> SEQ ID NO 8
<211> LENGTH: 579
<212> TYPE: DNA
<213> ORGANISM: Fusarium cf. equiseti

<400> SEQUENCE: 8
tactgggact gctgcaaacc ttcttgctct tggggcggca aggctaaagt caacgctccc     60
gctctgactt gtgacaacaa ggacaacccc atcaccaaca ccaactctgt caacggttgt    120
gagggtggcg ttctgcttta tgcttgcacc aactactctc cttgggccgt caacgacgat    180
cttgtctatg gtttcactgc tactaagctt gctggtggca ccgaggccag ctggtgctgt    240
gcttgttatg cgtatgtctc agtcgctctg atacatcatc ccgtgttttc atgctaactg    300
tatctctctc agtctcacct ttacgaccgg tccagtgaag ggcaagaaga tgattgtcca    360
gtccaccaac actggaggcg atcttggtga caaccacttc gatcttatga tgcccggcgg    420
cggagtcggt atcttcgacg gatgcacctc tcagttcgga aaggcccttg gtggtgctca    480
gtacggcggc atctcctctc gaagcgaatg tgatagcttc cccgagctgc tcaaggatgg    540
gtgccactgg cgatttgact ggttccaaaa cgccgataa                            579

<210> SEQ ID NO 9
<211> LENGTH: 638
<212> TYPE: DNA
<213> ORGANISM: Geomyces pannorum
<220> FEATURE:
<221> NAME/KEY: misc_feature
<222> LOCATION: (450)..(450)
<223> OTHER INFORMATION: n is a, c, g, or t

<400> SEQUENCE: 9
tactgggact gctgcaaacc gtcttgcggc tggacaggca aggccaccct caccagcggc     60
cccgtgcagt cctgtgacaa gaacgacaac gtgctcgcag acccagccac caagtccgca    120
tgcgacaatg gtggcccggc gttcatgtgc tcgaatgaga gtccgtgggc cgtctcggac    180
agtttggcgt atggatacgc cgcggtgtcg attgcgggtg gaacggaggc gagctggtgc    240
tgtgcttgct acgagttgac gtttacgagc ggcccggtgt cgggcaagaa gatgattgtg    300
caggcgacta atacgggtgg tgatcttggc cagaatcact tcgatatcgg cgtgcgtatt    360
ccatttccct cgccccttcc taccccttaa ctttctttca atactccttc ccaccagctt    420
ctgaaccgca tttatataag aatcacccan ctaacacccc ccagatgccc ggcggcggct    480
tcggcatctt caacgcctgc accccccaat acggcacccc ctccgccggc tggggcgccc    540
aatacggcgg catctcttcc cgcagccaat gcgacgcctt ccctgagaaa ctcaaggcgg    600
gatgctactg gcgcttcgac tggtttcaaa acgccgat                            638

<210> SEQ ID NO 10
<211> LENGTH: 636
<212> TYPE: DNA
<213> ORGANISM: Geomyces pannorum

<400> SEQUENCE: 10
tactgggact gctgcaaacc gtcctgcgcc tggacaggca aggcctcctt gacgagcggc     60
cccgtgcagg cctgtgacaa gaacgacaac gtgctcgccg acgcagatac caagtccgcc    120
tgcgacaacg gcggcccagc ctacatgtgc tctgatgaga gccatgggc cgtctcggac     180
```

| | |
|---|---:|
| agcctggcgt atggatacgc cgcggtgtcg atcgcgggcg ggacggaggc gagctggtgc | 240 |
| tgtgcctgct acgagttgac gtttacgagc ggcccggtgt ctggcaagaa gatgatcgtg | 300 |
| caggcgacga atacgggtgg tgaccttggc cagaatcaat tcgatctcgg cgtgcgtata | 360 |
| ccattcctcc ctccttcccc tcgaacgtcc cttcgcattc cccctccac cagttcctac | 420 |
| acctaattta cacacgaatt ccccccact aacgcccct agatgcccgg cggcggcttc | 480 |
| ggcctcttca acgcctgcac cccccagtac ggcacgcccc ccaccggctg ggcgcccaa | 540 |
| tacggcggta tctcctcgcg gagccagtgc gacgccttcc ccacggccct caaagccggc | 600 |
| tgctactggc gcttcgactg gttccagaac gcggac | 636 |

<210> SEQ ID NO 11
<211> LENGTH: 590
<212> TYPE: DNA
<213> ORGANISM: Geomyces pannorum

<400> SEQUENCE: 11

| | |
|---|---:|
| tactgggact gctgcaaacc gtcctgcggc tgggccgaca aagcagactt cgtcgacaag | 60 |
| tctccagtcc aatcatgcga taaaaacgca atccgctgc tagataattc caggggact | 120 |
| ggttgcaatg gcggcaatgc tttcggatgt gcgtcaaact cgccgtgggc cgttaatgac | 180 |
| acgttctcct acggcttcgt gggcactttc ctcgttggcg gcgacgagtc tagctggtgc | 240 |
| tgtagctgct accaattgaa ctttaccagc ggggcagtca agggcaaatc aatgattgtg | 300 |
| caagcctcga acacgaatta cgattccccg aacgcgaatg tctttactct tggtgtacgt | 360 |
| tgctcattct tccccagagc gagcgagtca cgcccgtact aatgccatt atcagatacc | 420 |
| tggtgggaat actagctacg ctggcgcgtg tgctctcgaa tacagtgtcc caaattctgt | 480 |
| gttcggcacg gaaaatgtgg gcgtgtcaaa tcgcaccgac tgtgacaatc ttcccgcagc | 540 |
| actgaagcct ggttgccagt ggcggttcga ctggttccag aatgcggcat | 590 |

<210> SEQ ID NO 12
<211> LENGTH: 1036
<212> TYPE: DNA
<213> ORGANISM: Geomyces pannorum
<220> FEATURE:
<221> NAME/KEY: Intron
<222> LOCATION: (445)..(565)

<400> SEQUENCE: 12

| | |
|---|---:|
| atggctctct ccaagctcac tctcctagcc ctcctccctc tctttctcgc taccccctca | 60 |
| ctcgccgcct caggcaatgg gaaaacaacc cgctactggg actgttgcaa gccctcctgc | 120 |
| gcctggtcag gcaaggcctc attcaaaacc ggtcccgtgc agtcctgtga caagggcgac | 180 |
| aatgtgctcg cagacgcaga caccaagtcc gcatgcgaca acggtggccc agcctttatg | 240 |
| tgctccgatg agagcccatg ggccgtctca gacagcctgg cctatggatt cgctgcggtg | 300 |
| tccatatcgg gtggcactga ggcgagctgg tgctgtgctt gctacgagtt gacgttcacg | 360 |
| agcggcccag tgtcaggcaa gaagatggtc gtgcaggcga caaatacggg tggtgaccttt | 420 |
| ggccagaatc actttgatat cggcgtacgt ataccgtttc tgtcctcgtc tttcttcttt | 480 |
| ctaccctcg acgtcccttc acatcccctc tccatcagct cctacacctc atttatataa | 540 |
| gaatccctca actaaccacc accagatgcc cggcggcggc ttcggcctct tcaacgcctg | 600 |
| cactccccaa tacggcacgc cttccaccgg ctggggaaat caatacggcg cctcacctc | 660 |
| gcggagccaa tgcgacgcct tccccaggcc cctcaaagcc ggttgctact ggaggttcga | 720 |
| ctggttccaa aacgccgaca acccttccgt cagcttcaag agcgttgcgt gtccgctggc | 780 |

-continued

```
cctcacgaat aaatcggggtt gtgtccgctc ggatgacacg ccaacgggag atggaaacgt    840
gccaacagct agtggagtgg ccccagcgag ctcgacgagt gcggggacga cgacgccgtc    900
gaccgggcca gggacaggag gagcgacagt ggcgaagtat gggcagtgtg ggggtcggg     960 gtggacgggg ggaacggttt gtgcgtctgg ctcgacttgc aaggcgacta accagtggta    1020
ctcgcagtgc ctgtaa                                                    1036
```

<210> SEQ ID NO 13
<211> LENGTH: 304
<212> TYPE: PRT
<213> ORGANISM: Geomyces pannorum

<400> SEQUENCE: 13

```
Met Ala Leu Ser Lys Leu Thr Leu Leu Ala Leu Leu Pro Leu Phe Leu
1               5                   10                  15

Ala Thr Pro Ser Leu Ala Ala Ser Gly Asn Gly Lys Thr Thr Arg Tyr
            20                  25                  30

Trp Asp Cys Cys Lys Pro Ser Cys Ala Trp Ser Gly Lys Ala Ser Phe
        35                  40                  45

Lys Thr Gly Pro Val Gln Ser Cys Asp Lys Gly Asp Asn Val Leu Ala
    50                  55                  60

Asp Ala Asp Thr Lys Ser Ala Cys Asp Asn Gly Pro Ala Phe Met
65                  70                  75                  80

Cys Ser Asp Glu Ser Pro Trp Ala Val Ser Asp Ser Leu Ala Tyr Gly
                85                  90                  95

Phe Ala Ala Val Ser Ile Ser Gly Gly Thr Glu Ala Ser Trp Cys Cys
            100                 105                 110

Ala Cys Tyr Glu Leu Thr Phe Thr Ser Gly Pro Val Ser Gly Lys Lys
        115                 120                 125

Met Val Val Gln Ala Thr Asn Thr Gly Gly Asp Leu Gly Gln Asn His
    130                 135                 140

Phe Asp Ile Gly Met Pro Gly Gly Gly Phe Gly Leu Phe Asn Ala Cys
145                 150                 155                 160

Thr Pro Gln Tyr Gly Thr Pro Ser Thr Gly Trp Gly Asn Gln Tyr Gly
                165                 170                 175

Gly Leu Thr Ser Arg Ser Gln Cys Asp Ala Phe Pro Gln Ala Leu Lys
            180                 185                 190

Ala Gly Cys Tyr Trp Arg Phe Asp Trp Phe Gln Asn Ala Asp Asn Pro
        195                 200                 205

Ser Val Ser Phe Lys Ser Val Ala Cys Pro Leu Ala Leu Thr Asn Lys
    210                 215                 220

Ser Gly Cys Val Arg Ser Asp Asp Thr Pro Thr Gly Asp Gly Asn Val
225                 230                 235                 240

Pro Thr Ala Ser Gly Val Ala Pro Ala Ser Ser Thr Ser Ala Gly Thr
                245                 250                 255

Thr Thr Pro Ser Thr Gly Pro Gly Thr Gly Gly Ala Thr Val Ala Lys
            260                 265                 270

Tyr Gly Gln Cys Gly Gly Ser Gly Trp Thr Gly Thr Val Cys Ala
        275                 280                 285

Ser Gly Ser Thr Cys Lys Ala Thr Asn Gln Trp Tyr Ser Gln Cys Leu
    290                 295                 300
```

<210> SEQ ID NO 14
<211> LENGTH: 966
<212> TYPE: DNA

```
<213> ORGANISM: Geomyces pannorum
<220> FEATURE:
<221> NAME/KEY: Intron
<222> LOCATION: (475)..(532)
<220> FEATURE:
<221> NAME/KEY: Intron
<222> LOCATION: (715)..(773)

<400> SEQUENCE: 14
atgacgaatc tatcaagatc cctacgccac accttcaccc tcctcctctt tgctctcgtt      60
ttctccagtg ttgatgcgat atccgacgta tttgggccgt ccactgcggt aacctcgcgg     120
tattgggact gctgtaagcc gtcctgcggc tgggccgaca aggagacttc gtcgacaag      180 tctccagtcc aatcgtgcga tatcaacgca atccgctgc tggatgttac ccaggggacc     240
ggttgcaatg gcggcaatgc gttcggatgt cgtcgaact cgccgtgggc cgtcaatgac     300
acgttctcct acggcttcgt gggcactttc ctcattggcg cgacgagtc cagctggtgc     360 tgcagctgct tccaattgaa ctttaccagc ggggcagtca aaggcaaatc gatgattgtg     420
caggcctcca acacgaatta cgattccca ggcgcgaatg tcttcactct tggtgtatgt     480
actcctttct ccgcagattg agagttacgc ccgtactaat gccttctatc agatacctgg     540
tggaaataca agctatgctg gcgcgtgtgc tatcgaatac aacgttccaa attctgtgtt     600
cggcacggaa aacgtgggcg tatccaatcg caccgactgt gatgactttc ccgcagcact     660
gaagcctggt tgccagtggc ggttcgactg gttcaaggac gccgtggagc caaagtgagt     720
acctatttta acccattcca agattcgcgc gaaatctaac gtgggaatta cagtgttgag     780
tataagcgcg tagcatgtcc gaaggttctc acggatatca cccactgcaa acgaaacgat     840
gacgatacgg ttgacgaaga tgcgatcaag gcgaattcac catccgcagc ttcaacactg     900
tcatcgatgg gccccacagc tatcactgtg ctgtttatgt ggtggatgct acaaacgctc     960
ggctaa                                                               966

<210> SEQ ID NO 15
<211> LENGTH: 282
<212> TYPE: PRT
<213> ORGANISM: Geomyces pannorum

<400> SEQUENCE: 15

Met Thr Asn Leu Ser Arg Ser Leu Arg His Thr Phe Thr Leu Leu Leu
1               5                   10                  15

Phe Ala Leu Val Phe Ser Ser Val Asp Ala Ile Ser Asp Val Phe Gly
                20                  25                  30

Pro Ser Thr Ala Val Thr Ser Arg Tyr Trp Asp Cys Cys Lys Pro Ser
            35                  40                  45

Cys Gly Trp Ala Asp Lys Gly Asp Phe Val Asp Lys Ser Pro Val Gln
        50                  55                  60

Ser Cys Asp Ile Asn Ala Asn Pro Leu Leu Asp Val Thr Gln Gly Thr
65                  70                  75                  80

Gly Cys Asn Gly Gly Asn Ala Phe Gly Cys Ala Ser Asn Ser Pro Trp
                85                  90                  95

Ala Val Asn Asp Thr Phe Ser Tyr Gly Phe Val Gly Thr Phe Leu Ile
                100                 105                 110

Gly Gly Asp Glu Ser Ser Trp Cys Cys Ser Cys Phe Gln Leu Asn Phe
            115                 120                 125

Thr Ser Gly Ala Val Lys Gly Lys Ser Met Ile Val Gln Ala Ser Asn
        130                 135                 140

Thr Asn Tyr Asp Ser Pro Gly Ala Asn Val Phe Thr Leu Gly Ile Pro
```

|  |  |  |  |  | 145 |  |  |  |  | 150 |  |  |  |  | 155 |  |  |  |  | 160 |

Gly Gly Asn Thr Ser Tyr Ala Gly Ala Cys Ala Ile Glu Tyr Asn Val
                    165                 170                 175

Pro Asn Ser Val Phe Gly Thr Glu Asn Val Gly Val Ser Asn Arg Thr
                180                 185                 190

Asp Cys Asp Asp Phe Pro Ala Ala Leu Lys Pro Gly Cys Gln Trp Arg
            195                 200                 205

Phe Asp Trp Phe Lys Asp Ala Val Glu Pro Ser Val Glu Tyr Lys Arg
        210                 215                 220

Val Ala Cys Pro Lys Val Leu Thr Asp Ile Thr His Cys Lys Arg Asn
225                 230                 235                 240

Asp Asp Asp Thr Val Asp Glu Asp Ala Ile Lys Ala Asn Ser Pro Ser
                245                 250                 255

Ala Ala Ser Thr Leu Ser Ser Met Gly Pro Thr Ala Ile Thr Val Leu
            260                 265                 270

Phe Met Trp Trp Met Leu Gln Thr Leu Gly
        275                 280

<210> SEQ ID NO 16
<211> LENGTH: 1162
<212> TYPE: DNA
<213> ORGANISM: Fusarium cf. equiseti
<220> FEATURE:
<221> NAME/KEY: Intron
<222> LOCATION: (330)..(390)

<400> SEQUENCE: 16

```
atgcgttctt ttgctctcct cgccctagtc ggtcctcttg ccgtgagcgc tgcttctgga      60
agtggccact ctactcgata ctgggactgc tgcaagcctt cttgctcttg gagcggcaag     120
gctaaagtca acgctcccgc tctgacttgt gacaacaagg acaaccccat caccaacacc     180
aactctgtca acggttgtga gggtggcggt tctgcttatg cttgcaccaa ctactctcct     240
tgggccgtca acgacgatct tgcctatggt ttcactgcta ctaagcttgc tggtggcacc     300
gaggccagct ggtgctgtgc ttgttatgcg tatgtctcag tcgctctgat acatcatccc     360
gtgttttcat gctaactgta tctctctcag tctcaccttt acgaccggtc cagtgaaggg     420
caagaagatg attgtccagt ccaccaacac tggaggcgat cttggtgaca accacttcga     480
tcttatgatg cccggcggcg gagtcggtat cttcgacgga tgcacctctc agttcggaaa     540
ggcccttggt ggtgctcagt acggcggcat ctcctctcga agcgaatgtg atagcttccc     600
cgagctgctc aaggatgggt gccactggcg atttgactgg ttcaagaacg ccgacaaccc     660
tgacttcacc ttcgagcagg tccagtgccc caaggaactc cttgctatta gtggttgcaa     720
gcgtgacgac gattccagct cccctgcctt cagtgggaac accacaccca gcaaggctaa     780
gccgagtggt aagaagacta ctgctgctgc tcagcctcag aagaccgagc aggctgtccc     840
tgttgttcag aagccggctg ctactaagcc cgcctccgag cctgtcgttt ccaagcctgc     900
tgtctccaag cctgccgccg cggaccccac caaggttgtc agcaagccca agtcaacctc     960
aaaagtcggt ggaaccaaga ctcacaagga ctgccctgcc actaagccaa ccaagccggc    1020
tgctccccag aagtctgctg tcgctatgta ctaccagtgc ggtggttcca agtccgccta    1080
ccccgatggc aacctccctt gcgcttccgg aagcaagtgt gtcaagatga acgattacta    1140
ctctcagtgt gtccccaact aa                                              1162
```

<210> SEQ ID NO 17
<211> LENGTH: 366

<212> TYPE: PRT
<213> ORGANISM: Fusarium cf. equiseti

<400> SEQUENCE: 17

```
Met Arg Ser Phe Ala Leu Leu Ala Leu Val Gly Pro Leu Ala Val Ser
1               5                   10                  15

Ala Ala Ser Gly Ser Gly His Ser Thr Arg Tyr Trp Asp Cys Cys Lys
            20                  25                  30

Pro Ser Cys Ser Trp Ser Gly Lys Ala Lys Val Asn Ala Pro Ala Leu
        35                  40                  45

Thr Cys Asp Asn Lys Asp Asn Pro Ile Thr Asn Thr Asn Ser Val Asn
    50                  55                  60

Gly Cys Glu Gly Gly Gly Ser Ala Tyr Ala Cys Thr Asn Tyr Ser Pro
65                  70                  75                  80

Trp Ala Val Asn Asp Asp Leu Ala Tyr Gly Phe Thr Ala Thr Lys Leu
                85                  90                  95

Ala Gly Gly Thr Glu Ala Ser Trp Cys Cys Ala Cys Tyr Ala Leu Thr
            100                 105                 110

Phe Thr Thr Gly Pro Val Lys Gly Lys Lys Met Ile Val Gln Ser Thr
        115                 120                 125

Asn Thr Gly Gly Asp Leu Gly Asp Asn His Phe Asp Leu Met Met Pro
    130                 135                 140

Gly Gly Gly Val Gly Ile Phe Asp Gly Cys Thr Ser Gln Phe Gly Lys
145                 150                 155                 160

Ala Leu Gly Gly Ala Gln Tyr Gly Gly Ile Ser Ser Arg Ser Glu Cys
                165                 170                 175

Asp Ser Phe Pro Glu Leu Leu Lys Asp Gly Cys His Trp Arg Phe Asp
            180                 185                 190

Trp Phe Lys Asn Ala Asp Asn Pro Asp Phe Thr Phe Glu Gln Val Gln
        195                 200                 205

Cys Pro Lys Glu Leu Leu Ala Ile Ser Gly Cys Lys Arg Asp Asp Asp
    210                 215                 220

Ser Ser Phe Pro Ala Phe Ser Gly Asn Thr Thr Pro Ser Lys Ala Lys
225                 230                 235                 240

Pro Ser Gly Lys Lys Thr Thr Ala Ala Ala Gln Pro Gln Lys Thr Glu
                245                 250                 255

Gln Ala Val Pro Val Val Gln Lys Pro Ala Ala Thr Lys Pro Ala Ser
            260                 265                 270

Glu Pro Val Val Ser Lys Pro Ala Val Ser Lys Pro Ala Ala Ala Asp
        275                 280                 285

Pro Thr Lys Val Val Ser Lys Pro Lys Ser Thr Ser Lys Val Gly Gly
    290                 295                 300

Thr Lys Thr His Lys Asp Cys Pro Ala Thr Lys Pro Thr Lys Pro Ala
305                 310                 315                 320

Ala Pro Gln Lys Ser Ala Val Ala Met Tyr Tyr Gln Cys Gly Gly Ser
                325                 330                 335

Lys Ser Ala Tyr Pro Asp Gly Asn Leu Pro Cys Ala Ser Gly Ser Lys
            340                 345                 350

Cys Val Lys Met Asn Asp Tyr Tyr Ser Gln Cys Val Pro Asn
        355                 360                 365
```

<210> SEQ ID NO 18
<211> LENGTH: 1028
<212> TYPE: DNA
<213> ORGANISM: Geomyces pannorum
<220> FEATURE:

```
<221> NAME/KEY: Intron
<222> LOCATION: (445)..(557)

<400> SEQUENCE: 18
atggctctct ccaaacgcac cctcctcgcc ctcctcccct tcttcctagc cgtcccctcc      60
ctcgccgtct ccggcacagg caaaacaacc cgctactggg actgctgcaa gccgtcttgc     120
ggctggacag gcaaggccac cctcaccagc ggccccgtgc agtcctgtga caagaacgac     180
aacgtgctcg cagacccaga caccaagtcc gcatgcgaca atggtggccc ggcgttcatg     240
tgctcgaatg agagtccgtg gccgtctcg gacagtttgg cgtatggata cgccgcggtg      300
tcgattgcgg gtggaacgga ggcgagctgg tgctgtgctt gctacgagtt gacgtttacg     360
agcggcccgg tgtcgggcaa gaagatgatt gtgcaggcga ctaatacggg tggtgatctt     420
ggccagaatc acttcgatat cggcgtgcgt attccatttc cctcgcccct ttctacccct     480
taactttctt tcaatactcc ttcccaccag cttctgaacc gcatttatat aagaatcacc     540
caactaacac cccccagatg cccggcggcg gcttcggcat cttcaacgcc tgcacccccc     600
aatacggcac ccctccacc ggctggggcg cccaatacgg cggcatctct tcccgcagcc      660
aatgcgacgc cttccctgag aaactcaagg cgggatgcta ctggcgcttc gactggttcc     720
agaacgccga caaccctct gtcagcttcc agagcgtcgc ttgcccactg ctattacga      780 ataaatcagg ctgtgtgcgt gcggatgata agccgacggg gggtgggacg gtgccgacgg     840
tgagcggggg tgctcctccg gcgaccctcga cgggtccggg gacgacgacg ccatcgagtg     900
ggacggggaa tgggggacg gtggcgaagt atgcgcagtg tgggggaat gggtggacgg       960 gtggtacggt ttgtgaggcg gggtcgactt gcaaggctac taatgagtgg tatgcgcagt    1020
gcctgtaa                                                             1028

<210> SEQ ID NO 19
<211> LENGTH: 304
<212> TYPE: PRT
<213> ORGANISM: Geomyces pannorum

<400> SEQUENCE: 19

Met Ala Leu Ser Lys Arg Thr Leu Leu Ala Leu Leu Pro Phe Phe Leu
1               5                  10                  15

Ala Val Pro Ser Leu Ala Val Ser Gly Thr Gly Lys Thr Thr Arg Tyr
            20                  25                  30

Trp Asp Cys Cys Lys Pro Ser Cys Gly Trp Thr Gly Lys Ala Thr Leu
        35                  40                  45

Thr Ser Gly Pro Val Gln Ser Cys Asp Lys Asn Asp Asn Val Leu Ala
    50                  55                  60

Asp Pro Asp Thr Lys Ser Ala Cys Asp Asn Gly Gly Pro Ala Phe Met
65                  70                  75                  80

Cys Ser Asn Glu Ser Pro Trp Ala Val Ser Asp Ser Leu Ala Tyr Gly
                85                  90                  95

Tyr Ala Ala Val Ser Ile Ala Gly Gly Thr Glu Ala Ser Trp Cys Cys
            100                 105                 110

Ala Cys Tyr Glu Leu Thr Phe Thr Ser Gly Pro Val Ser Gly Lys Lys
        115                 120                 125

Met Ile Val Gln Ala Thr Asn Thr Gly Gly Asp Leu Gly Gln Asn His
    130                 135                 140

Phe Asp Ile Gly Met Pro Gly Gly Gly Phe Gly Ile Phe Asn Ala Cys
145                 150                 155                 160

Thr Pro Gln Tyr Gly Thr Pro Ser Thr Gly Trp Gly Ala Gln Tyr Gly
```

```
                        165                 170                 175
Gly Ile Ser Ser Arg Ser Gln Cys Asp Ala Phe Pro Glu Lys Leu Lys
            180                 185                 190

Ala Gly Cys Tyr Trp Arg Phe Asp Trp Phe Gln Asn Ala Asp Asn Pro
            195                 200                 205

Ser Val Ser Phe Gln Ser Val Ala Cys Pro Leu Ala Ile Thr Asn Lys
            210                 215                 220

Ser Gly Cys Val Arg Ala Asp Asp Lys Pro Thr Gly Gly Gly Thr Val
225                 230                 235                 240

Pro Thr Val Ser Gly Gly Ala Pro Pro Ala Thr Ser Thr Gly Pro Gly
            245                 250                 255

Thr Thr Thr Pro Ser Ser Gly Thr Gly Asn Gly Gly Thr Val Ala Lys
            260                 265                 270

Tyr Ala Gln Cys Gly Gly Asn Gly Trp Thr Gly Gly Thr Val Cys Glu
            275                 280                 285

Ala Gly Ser Thr Cys Lys Ala Thr Asn Glu Trp Tyr Ala Gln Cys Leu
            290                 295                 300
```

<210> SEQ ID NO 20
<211> LENGTH: 1026
<212> TYPE: DNA
<213> ORGANISM: Geomyces pannorum
<220> FEATURE:
<221> NAME/KEY: Intron
<222> LOCATION: (445)..(555)

<400> SEQUENCE: 20

```
atggctctct ccaagctcac cctcctcgcc ctcctcccct tcttcctcgc cgccccctcc      60
ctcgccgtct ccggcactgg ccaaacaacc cgctactggg actgctgcaa gccgtcctgc     120
gcctggacag gcaaggcctc cttgacgagc ggccccgtgc aggcctgtga caagaacgac     180
aacgtgctcg ccgacgcaga taccaagtcc gcctgcgaca cggcggccc agcctacatg      240 tgctctgatg agagcccatg ggccgtctcg gacagcctgg cgtatggata cgccgcggtg     300
tcgatcgcgg gcgggacgga ggcgagctgg tgctgtgcct gctacgagtt gacgtttacg     360
agcggcccgg tgtctggcaa gaagatgatc gtgcaggcga cgaatacggg tggtgacctt     420
ggccagaatc aattcgatct cggcgtgcgt ataccattcc tccctccttc ccctcgaacg     480
tcccttcgca ttccccctc caccagttcc tacacctaat ttacacacga attcccccc      540 actaacgccc cctagatgcc cggcggcggc ttcggcctct tcaacgcctg cacccccaa      600 tacggcacgc cctccaccgg ctggggcgcc caatacggcg gtatctcctc gcggagccag     660
tgcgacgcct tccccacggc cctcaaagcc ggctgctact ggcgcttcga ctggttccag     720
aacgccgaca cccgaccgt cagcttccag agcgtcgcgt gtccgctggc gctgacgaat     780
aaatcgggct gcgtgcgcgc ggatgatacg ccgacgggga gtggacggt gtcgacggcg     840 agtgggggag gggcggtgag ctcgacgagt gcggggacga cgacgccgtc gagcgggacg     900
gggactgggg gtgcgacggt ggcgaagttt gggcagtgtg gggggtcggg gtggacgggg     960
gggacgactt gtgcggctgg atcgacttgc caggtgaata ccagtggta ttcgcagtgc     1020 ttgtaa                                                               1026
```

<210> SEQ ID NO 21
<211> LENGTH: 304
<212> TYPE: PRT
<213> ORGANISM: Geomyces pannorum

<400> SEQUENCE: 21

```
Met Ala Leu Ser Lys Leu Thr Leu Leu Ala Leu Leu Pro Phe Phe Leu
1               5                   10                  15

Ala Ala Pro Ser Leu Ala Val Ser Gly Thr Gly Gln Thr Thr Arg Tyr
            20                  25                  30

Trp Asp Cys Cys Lys Pro Ser Cys Ala Trp Thr Gly Lys Ala Ser Leu
                35                  40                  45

Thr Ser Gly Pro Val Gln Ala Cys Asp Lys Asn Asp Asn Val Leu Ala
        50                  55                  60

Asp Ala Asp Thr Lys Ser Ala Cys Asp Asn Gly Pro Ala Tyr Met
65                  70                  75                  80

Cys Ser Asp Glu Ser Pro Trp Ala Val Ser Asp Ser Leu Ala Tyr Gly
                85                  90                  95

Tyr Ala Ala Val Ser Ile Ala Gly Gly Thr Glu Ala Ser Trp Cys Cys
                100                 105                 110

Ala Cys Tyr Glu Leu Thr Phe Thr Ser Gly Pro Val Ser Gly Lys Lys
                115                 120                 125

Met Ile Val Gln Ala Thr Asn Thr Gly Gly Asp Leu Gly Gln Asn Gln
130                 135                 140

Phe Asp Leu Gly Met Pro Gly Gly Gly Phe Gly Leu Phe Asn Ala Cys
145                 150                 155                 160

Thr Pro Gln Tyr Gly Thr Pro Ser Thr Gly Trp Gly Ala Gln Tyr Gly
                165                 170                 175

Gly Ile Ser Ser Arg Ser Gln Cys Asp Ala Phe Pro Thr Ala Leu Lys
                180                 185                 190

Ala Gly Cys Tyr Trp Arg Phe Asp Trp Phe Gln Asn Ala Asp Asn Pro
                195                 200                 205

Thr Val Ser Phe Gln Ser Val Ala Cys Pro Leu Ala Leu Thr Asn Lys
                210                 215                 220

Ser Gly Cys Val Arg Ala Asp Asp Thr Pro Thr Gly Ser Gly Thr Val
225                 230                 235                 240

Ser Thr Ala Ser Gly Gly Gly Ala Val Ser Ser Thr Ser Ala Gly Thr
                245                 250                 255

Thr Thr Pro Ser Ser Gly Thr Gly Thr Gly Gly Ala Thr Val Ala Lys
                260                 265                 270

Phe Gly Gln Cys Gly Gly Ser Gly Trp Thr Gly Thr Thr Cys Ala
                275                 280                 285

Ala Gly Ser Thr Cys Gln Val Asn Asn Gln Trp Tyr Ser Gln Cys Leu
290                 295                 300
```

<210> SEQ ID NO 22
<211> LENGTH: 969
<212> TYPE: DNA
<213> ORGANISM: Geomyces pannorum
<220> FEATURE:
<221> NAME/KEY: Intron
<222> LOCATION: (475)..(535)
<220> FEATURE:
<221> NAME/KEY: Intron
<222> LOCATION: (718)..(776)

<400> SEQUENCE: 22

```
atgacgaatc tatcaaggtc cctacgccac atcttcgccg tcctcctctt tgctctcgtt    60
ttctcctgtg ttgatgctgt gtccgacgtg tttgggccct ccaccgcggt aacatctcgg   120
tattgggact gctgcaagcc gtcctgcggc tgggccgaca agcagacttc gtcgacaag   180 tctccagtcc aatcatgcga taaaaacgca aatccgctgc tagataattc ccaggggact  240
```

```
ggttgcaatg gcggcaatgc tttcggatgt gcgtcaaact cgccgtgggc cgttaatgac      300
acgttctcct acggcttcgt gggcactttc ctcgttggcg gcgacgagtc tagctggtgc      360
tgtagctgct accaattgaa ctttaccagc ggggcagtca agggcaaatc aatgattgtg      420
caagcctcga acacgaatta cgattccccg aacgcgaatg tctttactct tggtgtacgt      480
tgctcattct tccccagagc gagcgagtca cgcccgtact aatgccattt atcagatacc      540
tggtgggaat actagctacg ctggcgcgtg tgctctcgaa tacagtgtcc caaattctgt      600
gttcggcacg gaaaatgtgg gcgtgtcaaa tcgcaccgac tgtgacaatc ttcccgcagc      660
actgaagcct ggttgccagt ggcggttcga ctggttcaag gacactgagg gaccaaagtg      720
agtaccatt ctaacccatt ttaacaatcc cccgttatct aacggtgaaa ttacagtgtc       780
gagtataagc gcgtgacatg cccaaaggtt ctcacggata tcacccactg caaacgagag      840
gatgacgaaa gagtcgaaga agatgcgatc aaggccaatt caccatctgc ggcttcagca      900
ctgccgtcta tggtccctac agctatctct gcaatattta tgtggtggat gctacaaacg      960
ctcggctga                                                              969
```

<210> SEQ ID NO 23
<211> LENGTH: 282
<212> TYPE: PRT
<213> ORGANISM: Geomyces pannorum

<400> SEQUENCE: 23

```
Met Thr Asn Leu Ser Arg Ser Leu Arg His Ile Phe Ala Val Leu Leu
1               5                   10                  15

Phe Ala Leu Val Phe Ser Cys Val Asp Ala Val Ser Asp Val Phe Gly
            20                  25                  30

Pro Ser Thr Ala Val Thr Ser Arg Tyr Trp Asp Cys Cys Lys Pro Ser
        35                  40                  45

Cys Gly Trp Ala Asp Lys Ala Asp Phe Val Asp Lys Ser Pro Val Gln
    50                  55                  60

Ser Cys Asp Lys Asn Ala Asn Pro Leu Leu Asp Asn Ser Gln Gly Thr
65                  70                  75                  80

Gly Cys Asn Gly Gly Asn Ala Phe Gly Cys Ala Ser Asn Ser Pro Trp
                85                  90                  95

Ala Val Asn Asp Thr Phe Ser Tyr Gly Phe Val Gly Thr Phe Leu Val
            100                 105                 110

Gly Gly Asp Glu Ser Ser Trp Cys Cys Ser Cys Tyr Gln Leu Asn Phe
        115                 120                 125

Thr Ser Gly Ala Val Lys Gly Lys Ser Met Ile Val Gln Ala Ser Asn
    130                 135                 140

Thr Asn Tyr Asp Ser Pro Asn Ala Asn Val Phe Thr Leu Gly Ile Pro
145                 150                 155                 160

Gly Gly Asn Thr Ser Tyr Ala Gly Ala Cys Ala Leu Glu Tyr Ser Val
                165                 170                 175

Pro Asn Ser Val Phe Gly Thr Glu Asn Val Gly Val Ser Asn Arg Thr
            180                 185                 190

Asp Cys Asp Asn Leu Pro Ala Ala Leu Lys Pro Gly Cys Gln Trp Arg
        195                 200                 205

Phe Asp Trp Phe Lys Asp Thr Glu Gly Pro Ser Val Gly Tyr Lys Arg
    210                 215                 220

Val Thr Cys Pro Lys Val Leu Thr Asp Ile Thr His Cys Lys Arg Glu
225                 230                 235                 240

Asp Asp Glu Arg Val Glu Glu Asp Ala Ile Lys Ala Asn Ser Pro Ser
```

```
                        245                 250                 255
Ala Ala Ser Ala Leu Pro Ser Met Val Pro Thr Ala Ile Ser Ala Ile
            260                 265                 270

Phe Met Trp Trp Met Leu Gln Thr Leu Gly
            275                 280
```

FUNGAL ENDOGLUCANASES, THEIR PRODUCTION AND USE

RELATED APPLICATION DATA

This application is a National Stage Application under 35 U.S.C. 371 of co-pending PCT application PCT/FI2009/051043 designating the United States and filed Dec. 28, 2009; which claims the benefit of FI patent application number 20086253 and filed Dec. 30, 2008 each of which are hereby incorporated by reference in their entireties.

FIELD OF THE INVENTION

The invention relates to novel fungal endoglucanases, their production and means for their production. The invention further relates to enzyme preparations comprising at least one novel endoglucanase as well as to processes for treating cellulosic material therewith. Still further the invention relates to detergent compositions and animal feed comprising the endoglucanases.

BACKGROUND OF THE INVENTION

Cellulases are amongst the most widely used enzymes in industry. They are generally applied in textile industry, detergent industry, pulp and paper industry, feed and food industry, including baking and in hydrolysis of lignocellulosic material for, e.g., bioethanol production etc. The practical use of cellulases is hampered by the nature of the cellulase compositions, which often are enzyme mixtures having a variety of activities and substrate specificities. For this reason, efforts have been made to obtain cellulases having only the desired activities. The unique properties of each cellulase make some more suitable for certain purposes than others.

In fabric treatment cellulases attack the chains of cellulose molecules that form the cotton fibers, thereby affecting the characteristics of the fabric.

In textile industry a "stone washed" or abraded look has been denim producers' interest in recent years. Traditional stone washing with pumice stones reduces the strength of fabric and burdens the laundering apparatuses. The trend has been towards enzymatic denim finishing processes and cellulases have replaced or are being used together with pumice stones to give the fabric its desired "worn" look. Controlled enzyme treatments result in less damage to the garments and machines and eliminate the need for disposal of stones.

Additionally, textile industry uses cellulases in biofinishing, i.e. to create permanent improvement of depilling, and to improve pilling resistance, clear surface structure by reduced fuzz, improve textile handle, such as softness, smoothness and a silkier feel, improve drapability and brighter colors of the textile and improve moisture absorbability.

Cellulases comprise a catalytic domain/core (CD) expressing cellulase activity. In addition to the catalytic domain the cellulase molecule may comprise one or more cellulose binding domains (CBDs), also named as carbohydrate binding domains/modules (CBD/CBM), which can be located either at the N- or C-terminus of the catalytic domain. CBDs have carbohydratebinding activity and they facilitate the enzymatic action on solid substrates. The catalytic core and the CBD are typically connected via a flexible and highly glycosylated linker region.

Cellulases that attack primarily on the surface of the fiber are especially useful in stone washing of denim dyed with Indigo dye, as the dye is located on the surface of the fiber. Cellulases applied in denim treatment are usually divided into two main groups: acid and neutral cellulases. Acid cellulases typically operate at pH 4.0-5.5 and the neutral cellulases in the range of pH 6-8. Acid cellulases are especially used in biofinishing (depilling) and also in denim treatment (biostoning) while neutral celluases are typically used in denim applications.

Endoglucanases (EGs) are one of the three types of cellulases generally needed for the biological conversion of cellulose to glucose. Some naturally occurring endoglucanases have a cellulose-binding domain (CBD), while others do not. Endoglucanases are widely used in textile, detergent, bioethanol and pulp and paper industry.

Cellulases including endoglucanases may be classified into various glycosyl hydrolase families according their primary sequence, supported by analysis of the three dimensional structure of some members of the family (Henrissat 1991, Henrissat and Bairoch 1993, 1996). For example glycosyl hydrolase families 5, 7, 12 and 45 contain endoglucanases. Most of the acid textile cellulases belong to family 5, whereas most of the neutral textile cellulases are of family 12 or 45.

The wide spectrum of industrial uses for endoglucanases has established a need for commercial endoglucanase products showing desired performance at desired conditions such as pH and temperature ranges.

The majority of the industrially used enzymes work better at elevated temperatures, usually about >50° C., but for energy saving reasons, better color fastness and reduction of shrinkage of garments there is a need for enzymes with good performance at lower temperature levels i.e. <50° C., for example about 30 to 40° C., or even 20 to 40° C. Such cold active enzymes have been described e.g. in bacteria, especially in *Bacillus*. However, production of bacterial enzymes for industrial applications is complicated and laborious compared to the production of fungal enzymes. Still there is very little knowledge about possible cold active fungal endoglucanases.

To our knowledge no cold acting endoglucanase of family 45 has been described so far.

An endoglucanase of the Cel45 family is disclosed in U.S. Pat. No. 5,610,129, which describes dye transfer inhibiting compositions containing a *Humicola insolens* kd43 cellulase. Its thermal properties are not disclosed.

*Gibberella zeae* Cel45 enzymes have not been proposed to be used in textile finishing.

U.S. Pat. No. 7,256,032 describes Cel45 cellulases having good performance in textile finishing. Performance in denim finishing is optimal at 60° C., and the lowest temperature measured is 40° C. with less than 50% of the optimal activity.

US20071070003 describes cellulase preparations performing well e.g. in laundry compositions, biopolishing newly manufactured textiles and providing an abraded look for cellulosic fabric. None of the enzymes described shows an advantageous performance at low temperatures.

Thus there is a continuous need for new and advantageous cellulases having desired properties and thermal profiles. The present invention meets this need.

BRIEF DESCRIPTION OF THE INVENTION

The present invention now provides novel endoglucanases of the cel45 family, with a unique thermal profile shown by having good performance also at low temperatures. The unique thermal properties mean that no remarkable decrease in performance can be seen when the temperature is below 50° C. e.g. about 40° C., about 30° C. or even about 20° C. The endoglucanases are useful in different cellulase applications such as fabric treatment, especially denim treatment and depilling. Contrary to previously described depilling enzymes, which generally are acid cellulases, the novel endoglucanases perform well also at relatively neutral pH. This enables biofinishing treatment simultaneously with dyeing, leading to considerable savings. Also the color fastness is often better at neutral conditions.

The present invention provides a fungal endoglucanase polypeptide, which belongs to glycosyl hydrolase family 45, and which shows substantial performance at low temperatures. The invention further provides an enzyme preparation comprising said endoglucanase, and detergent compositions and animal feed comprising said enzyme or enzyme preparation.

In particular the invention is directed to endoglucanases that comprise an amino acid sequence having at least 65% sequence identity to SEQ ID NO: 13, at least 48% sequence identity to SEQ ID NO: 15, at least 87% sequence identity to SEQ ID NO: 17, at least 62% sequence identity to SEQ ID NO: 19, at least 59% sequence identity to SEQ ID NO: 21 or at least 49% sequence identity to SEQ ID NO: 23, or an enzymatically active fragment thereof.

The invention is further directed to an isolated polynucleotide selected from the group consisting of:

a) a nucleotide sequence having SEQ ID NO: 12, 14, 16, 18, 20 or 22, or a sequence encoding the endoglucanase polypeptide described above, b) a complementary strand of a) or c) a sequence that is degenerate as a result of the genetic code to anyone of the sequences of a) or b).

The invention is still further directed to an expression vector comprising said polynucleotide, a host cell comprising said expression vector, and an *E. coli* strain having accession number DSM 18916, DSM 19171, DSM 19173, DSM 18915, DSM 18917, or DSM 19170.

Still further the invention provides a method for the production of the endoglucanase polypeptide, comprising the steps of transforming a host cell with an expression vector encoding said polypeptide, and culturing said host cell under conditions enabling expression of said polypeptide, and optionally recovering and purifying said polypeptide.

Finally the invention provides a process for treating cellulosic material, wherein said process comprises contacting the cellulosic material with the endoglucanase polypeptide or enzyme preparation of the invention.

Specific embodiments of the invention are set forth in the dependent claims. Other objects, details and advantages of the present invention will become apparent from the following drawings, detailed description and examples. It should be understood, however, that the embodiments given in the description, drawings and in the examples are for illustrative purposes only, and that various changes and modifications are possible within the scope of the claims.

DETAILED DESCRIPTION OF THE INVENTION

Figure 1:
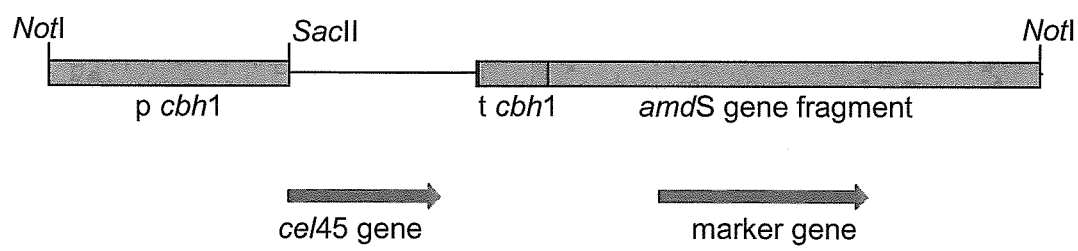
FIG. 1 is a schematic picture of the expression cassettes used in the transformation of *Trichoderma reesei* protoplasts for overproducing the recombinant Cel45 proteins.

The invention is based on studies, where a fungal culture collection was screened for low-temperature cellulolytic activity. Fungal strains were cultivated at 20° C. for 3-7 days using various production media. Supernatants were recovered and cellulolytic activity against carboxymethylcellulose (CMC) and hydroxyethylcellulase (HEC) at temperatures 30° C. and 50° C. was tested to screen low temperature profiles. The most favorable strains were further tested in small-scale biostoning applications after cultivation at 20° C. for 4-7 days. After preliminary screening four strains were selected for construction of genomic libraries, and the libraries were further screened for cel45 genes with probes amplified using degenerate primers. Positive phage clones were subcloned to bacterial vectors and confirmed by sequencing before deposition at DSMZ. For production of the Cel45 enzymes the genes encoding desired activities were fused to *Trichoderma reesei* cbh1/cel7A promoter. Transcription termination was ensured by a *T. reesei* cbh1/cel7A terminator, and an amdS marker was used for screening positive clones. Linear expression cassettes were isolated from the vector backbone and transformed into *T. reesei* protoplasts having major cellulases deleted. Purified transformants were cultured for 7 days in cellulase inducing media and endoglucanase activity was tested from the culture supernatant. Thermal and pH properties were also tested. Material for large-scale application was obtained by laboratory bioreactor cultivations at 28° C. lasting for 3-4 days followed by filtration and concentration when needed.

Culture supernatants were tested in denim treatment in different temperatures using two commercial cel45 preparations as references in a washing machine. The resulting biostoning effect was evaluated using color reflectance measurement. Surprisingly it was found that temperature profiles measured in application were different from those received in primary characterization in test tubes. In addition pH properties of the samples were tested in denim application. Further, the depilling/defuzzing effect on yarn cotton fleece was tested in a washing machine with different dosages of enzyme and compared to a prior art sample. Surprisingly at low temperature fuzz-free surface was obtained using a lower dosage than what could be expected based on tests in denim treatment.

The present invention provides novel fungal endoglucanase polypeptides of glycosyl hydrolase family 45 with substantial performance at low temperatures. Polypeptide and protein as used herein are synonyms.

"Fungal" in this context means that the endoglucanase or the polynucleotide encoding it may be derived from a fungus, and especially from a filamentous fungus, such as *Geomyces* or *Fusarium*. According to a specific embodiment of the invention the endoglucanase is derived from *G. pannorum* or *F.* cf *equiseti*, most preferably from *G. pannorum* RF 6293 (CBS 119567), *F.* cf. *equiseti* RF6318 (CBS119568), *G. pannorum* RF6546 (CBS119958), or *G. pannorum* RF6608 (CBS119962).

The term "derived from" in connection with a microorganism source means that the polypeptide may naturally be produced by said specific microorganism source, or the polynucleotide encoding the polypeptide may be isolated from said microorganism source, and optionally expressed in a host cell into which the polynucleotide or a synthetized version thereof, possibly using alternative codons, from said microorganism source encoding the polypeptide has been introduced. However, it does not exclude minor modifications of the sequence e.g. by substitution, deletion, and/or insertion of one or a few amino acids/nucleotides as long as the enzymatic activity of the encoded and secreted protein is retained.

"Endoglucanase" ("EG") in connection with the present invention refers to enzymes classified as E.C. 3.2.1.4. They are 1,4-beta-D-glucan 4-glucanohydrolases and catalyze endohydrolysis of 1,4-beta-D-glycosidic linkages in polymers of glucose such as cellulose. Some endoglucanases may also hydrolyse e.g. 1,4-linkages in beta-D-glucans also containing 1,3-linkages. They may therefore also be classified as endo-1,3(4)-beta-glucanases (E.C. 3.2.1.6). Thus, an enzyme may catalyze reactions on several substrates and can belong to multiple classes. The endoglucanases of the invention may optionally contain a signal sequence, and one or more cellulose binding domains (CBDs) linked to the catalytic domain/core (CD).

"Glycosyl hydrolase family 45" refers to the glycosyl hydrolase family as defined by Henrissat 1991, and Henrissat and Bairoch 1993, 1996, which are incorporated herein by reference. The gene encoding family 45 cellulase is called cel45 and the encoded protein is called Cel45.

The endoglucanases of the invention show substantial performance at low temperature. "Substantial performance" in this context means that the enzymes show excellent performance when applied in at least one type of cellulase application process such as e.g. biostoning and/or biofinishing of textiles, or in washing. The unique temperature profiles of the novel endoglucanases may be illustrated by their "30:50 ratio" in denim application, which indicates relative performance (%) at 30° C. compared to 50° C. Preferably the 30:50 ratio is at least 72%, more preferably at least 80%, and most preferably at least 90% or 95%. Alternatively the temperature profile may be illustrated by a "40:OT" ratio, which means relative performance (%) at 40° C. compared to optimal temperature. Preferably the 40:OT ratio is at least 80%, more preferably at least 90%, and most preferably at least 95%.

"Cold active" or "low temperature" as used herein refers to a temperature of ≤50° C., especially ≤45° C., preferably ≤40° C., including ≤30° C.

According to one embodiment of the invention, the endoglucanase comprises an amino acid sequence having at least 65% sequence identity to SEQ ID NO: 13, at least 48% sequence identity to SEQ ID NO: 15, at least 87% sequence identity to SEQ ID NO: 17, at least 62% sequence identity to SEQ ID NO: 19, at least 59% sequence identity to SEQ ID NO: 21 or at least 49% sequence identity to SEQ ID NO: 23, or an enzymatically active fragment thereof. Preferably the endoglucanase comprises an amino acid sequence having at least 90%, preferably at least 95% and most preferably at least 98% or 99% sequence identity to SEQ ID NO: 13, 15, 17, 19, 21 or 23, or an enzymatically active fragment thereof.

As used in the present context the term "identity" refers to the global identity between two amino acid sequences compared to each other from the first amino acid encoded by the corresponding gene to the last amino acid. For the purposes of the present invention identity is preferably determined by means of known computer programmes using standard algorithms. An example of such a programme is Clone Manager Suite, a programme that includes the programme part Align Part and is sold by Scientific & Educational Software, Durham, N.C., USA. According to present invention, the programme version "Clone Manager 7 Align Plus 5" including the functions "Compare Two Sequences/Global/Compare DNA sequences" was especially used for determining the degree of identity. In this case algorithms available from the following sources were used: Hirschberg, D. S. (1975) A linear space algorithm for computing longest common subsequences, Commun. Assoc. Comput. Mach. 18: 341-343; Myers, E. W. and W. Miller. (1988) Optimal alignments in linear space, CABIOS 4:1, 11-17; Chao, K-M, W. R. Pearson and W. Miller. (1992) Aligning two sequences within a specified diagonal band, CA-BIOS 8:5, 481-487. The man skilled in the art is aware of the fact that results are comparative only when aligning corresponding domains of the sequence. Consequently comparison of e.g. cellulase sequences including CBD or signal sequences with sequences lacking those elements are excluded as not being meaningful.

"Enzymatically active fragment" refers to part of a specific amino acid sequence that is long enough to have the desired enzymatic activity. In other words a fragment may be e.g. only the mature part of the polypeptide or even a subsequence of the mature part. It may or may not contain a linker and CBD domain. More specifically enzymatic activity refers to cellulase activity that has catalytic ability to hydrolyse cellulose or derivatives thereof, such as endoglucanase or beta-glucanase activity. In addition to endoglucanase and/or beta-glucanase activity, some of the cellulases may further have hemicellulase and/or xylanase activity. The enzymatic activity may be determined as described in Example 1.

The polynucleotides of the invention may be either DNA or RNA. According to one embodiment of the invention the endoglucanases are encoded by a polynucleotide having SEQ ID NO: 12, 14, 16, 18, 20 or 22, or a fragment thereof long enough to encode an enzymatically active endoglucaease. Preferably the endoglucanases are encoded by a polynucleotide similar to that carried by E. coli DSM 18916, DSM 19171, DSM 19173, DSM 18915, DSM 18917, or DSM 19170.

The endoglucanases of the invention are preferably recombinant proteins. They are conveniently prepared by generally known recombinant DNA technology in a heterologous or homologous host. Preferably the endoglucanase is overexpressed in a fungal host. Briefly the polynucleotide encoding the endoglucanase is cloned and inserted into an expression vector, transformed into a host cell and expressed.

An "expression vector" is a cloning plasmid or vector capable of expressing DNA encoding the endoglucanase proteins after transformation into a desired host. When a fungal host is used, the gene of interest is preferably provided to a fungal host as part of a cloning or expression vehicle that integrates into the fungal chromosome, or allows the gene of interest to integrate into the host chromosome. Other sequences that are part of the cloning vehicle or expression vehicle may also be integrated with said DNA during the integration process. In addition, in fungi the expression vector or parts thereof can be targeted into predetermined loci. Alternatively, the desired gene can be provided as an autonomously replicating plasmid.

The DNA encoding the endoglucanase proteins is preferably placed under the control of (i.e., operably linked to) certain control sequences such as promoter sequences provided by the vector. Upon transformation these control sequences integrate into the host genome with the gene of interest. Alternatively, the control sequences can be those at the integration site.

The expression control sequences of an expression vector will vary depending on whether the vector is designed to express a certain gene in a prokaryotic or in a eukaryotic host. Expression control sequences can contain transcriptional regulatory elements such as promoters, enhancer elements, and transcriptional termination sequences, and/or translational regulatory elements, such as translational initiation and termination sites.

A polynucleotide molecule, such as DNA, is said to be capable of expressing a polypeptide, if it contains expression control sequences, which contain transcriptional regulatory information and such sequences are operably linked to the nucleotide sequence, which encodes the polypeptide.

An operable linkage is a linkage in which a sequence is connected to a regulatory sequence (or sequences) in such a way as to place expression of the sequence under the influence or control of the regulatory sequence. Two DNA sequences (such as a promoter region sequence linked to the 5' end of the protein encoding sequence) are said to be operably linked if function of the promoter results in transcription.

The vectors of the invention may further comprise other operably linked regulatory elements, such as enhancer sequences.

In a preferred embodiment, genetically stable transformants are constructed, whereby the DNA encoding the proteins is integrated into the host chromosome by transformation with a vector, which may harbor sequences promoting integration of said vector into the chromosome.

Cells that have stably integrated DNA encoding the endoglucanase proteins into their chromosomes may be selected e.g. by introduced marker(s), homologous or heterologous, which allow for selection of host cells which contain the expression vector in the chromosome, for example the marker may provide biocide resistance, e.g., resistance to antibiotics, or heavy metals, such as copper, or markers complementing an auxotrophic mutation in the host chromosome, and the like. The selectable marker can for example be a selection gene directly linked to the DNA gene sequences to be expressed, or introduced into the same cell by co-transformation. Also other selection systems can be used.

Once the expression vector containing the DNA encoding the endoglucanase is prepared, it is introduced into an appropriate host cell by any of a variety of suitable means, including transformation as known in the art. After transformation, recipient cells are usually grown in an appropriate selective medium, which selects for the growth of transformed cells.

Suitable expression and production host systems are for example the production system developed for fungal hosts *Trichoderma* (EP 244 234), or *Aspergillus*, such as *A. oryzae* or *A. niger* (WO 97/08325 and WO 95/33386, U.S. Pat. No. 5,843,745, U.S. Pat. No. 5,770,418), or the production system developed for *Fusarium*, such as *F. oxysporum* (Malardier et al., 1989) or *Chrysosporium lucknowense*. According to a preferred embodiment of the invention partially cellulase and/or hemicellulase and/or protease deficient host strains can be used. Suitable production systems developed for bacteria include a production system developed for *Bacillus*, for example *B. subtilis, B. licheniformis, B. amyloliquefaciens* or for *E. coli*, or for an actinomycete *Streptomyces*. Suitable production systems developed for yeasts are systems developed for *Saccharomyces, Shizosaccharomyces, Pichia pastoris* or *Hansenula*. Production systems in other microbes including consolidated fermentative microbes for bioethanol production or in mammalian cells or in plants are also possible.

Expression of the cloned gene sequence(s) results in the production of the desired protein, or in the production of a fragment of this protein. This expression can take place in a continuous manner in the transformed cells, or in a controlled manner.

To obtain the enzyme preparations of the invention, the hosts having the desired properties (that is, hosts capable of expressing economically feasible quantities of the endoglucanase proteins) are cultivated under suitable conditions, and the desired enzymes are preferably secreted from the hosts into the culture medium, and optionally recovered from said culture medium by methods known in the art. Preferably the host for such production is a filamentous fungus, such as *Trichoderma* or *Aspergillus*, and especially *T. reesei*.

As used in the present context the "enzyme preparation" refers to any enzyme product, which contains at least one of the novel endoglucanases described herein. Thus, such an enzyme preparation may be a spent culture medium or filtrate. Spent culture medium means the culture medium of the host comprising the produced enzymes. Preferably the host cells are separated from said medium after the production. If desired, such preparations may be lyophilized or the enzymatic activity otherwise concentrated and/or stabilized for storage. If required, a desired enzyme may be isolated and further purified in accordance with conventional methods, such as filtration, extraction, precipitation, chromatography, affinity chromatography, electrophoresis, or the like.

However, it is an advantage of the invention that the culture medium with or without host cells may be utilized as an enzyme preparation as such without further purification, because the endoglucanase proteins can be secreted into the culture medium, and they display activity in the ambient conditions of the spent culture medium. The enzyme preparations are very economical to provide and use, because isolation of a specific enzyme from the culture medium is unnecessary.

In addition to one or more endoglucanase proteins, the enzyme preparations may comprise one or more other enzymes, which may be for example other cellulases, amylases, lipases, proteases, hemicellulases, xylanases, pectinases and/or oxidases such as laccases, peroxidases and catalases. Alternatively, before, during or after the treatment with the endoglucanase protein another enzyme treatment may be carried out. The enzyme treatment may comprise, for example, one or more amylase treatments (e.g. for desizing of denim), one or more cellulase treatments and/or one or more peroxidase and/or laccase treatments. It depends on the application what other enzymes are included in the enzyme preparation or used in the enzyme treatment.

In addition to the endoglucanase protein, the enzyme preparation may contain additives, such as stabilizers, buffers, preservatives, surfactants and/or culture medium components. Preferred additives are such, which are commonly used in enzyme preparations intended for the application, where the enzyme preparation is used.

The enzyme preparations may be provided as a liquid or as a solid, for example, as a dried powder or granular, especially non-dusting granules, or a stabilized liquid. It is envisioned that the enzyme preparations can be further enriched to satisfy the requirements of a specific utility in various applications e.g. in the textile industry. A mixture of enzyme activities secreted by a host can be advantageous in a particular industrial application, for example in biofinishing and biostoning.

The endoglucanase proteins and the preparations thereof are useful e.g. in textile, feed and food, e.g. baking applications, in biomass hydrolysis, e.g. in bioethanol production, and in plant oil, detergent, and pulp and paper industry. They may be used for treating any cellulosic material, such as textile material, plants or material of plant origin used in food or animal feed, plant material for oil extraction, or wood-derived mechanical or chemical pulp or secondary fiber. They may also be added into detergents e.g. to improve fabric care properties by antipilling, antigreying, color clarification and softening, ant to improve the textile cleaning effect, for instance soil removal. The detergent compositions further normally contain auxiliaries, such as surface active agents (anionic, non-ionic, cationic and ampholytic surfactants), builders and other optional ingredients such as anti-redeposition and soil suspension agents, optical brighteners, bleaching agents, dyes and pigments and hydrolases.

In the present context "cellulosic material" refers to any material comprising cellulose or derivatives thereof as a significant component. The cellulosic material is contacted with an effective amount of the protein under suitable conditions, such as appropriate pH, and temperature, and the reaction is allowed to continue for a time sufficient for the enzymatic reaction to take place. The described endoglucanases are preferably used at a temperature range of about 20-50° C., and more preferably about 30-50° C. Useful temperatures are ≤50° C., for example ≤45° C., or in some cases ≤40° C., or even ≤30° C. A suitable pH range is about 3-9, preferably about 4-8, and especially about 5-6.5.

The endoglucanases are especially useful in the treatment of textile materials, such as fabrics and garments or yarn. The textile material may be manufactured of natural cellulose containing fibers or man-made cellulose containing fibers or mixtures thereof, or a blend of synthetic fibers and cellulose containing fibers. Preferably the cellulose containing material is cotton, especially denim. By "denim" is meant, in connection of this invention, denim fabric, usually denim garments, particularly jeans. Advantageously the denim is Indigo dyed denim. Denim can also be treated with derivatives of Indigo or with Indigo together with some other dye, for example Indigo-dyed denim with sulphur bottom.

The described endoglucanases are especially useful in textile industry preferably in biostoning and biofinishing.

Stone washing has three steps: desizing, abrasion and after-treatment. The first step, the desizing process is normally the first wet treatment of jeans and means removal of starch or other sizing agents usually applied to the warp yarns to prevent damage during the weaving process. Alpha-amylases are used to remove starch-based sizing agents for improved and uniform wet processing. After desizing the jeans are normally rinsed with water or passed directly to the abrasion step.

The second step, abrasion, can be performed with enzymes or pumice stones or both. In all cases mechanical action is needed to remove the dye, and the treatment is usually carried out in washing machines, like drum washers. The term "abraded" means the appearance of denim fabric, when it has been treated by cellulase enzymes or stones, or both. Synonymous expressions are "stone washed look" or "worn look". As a result of uneven dye removal there are contrasts between dyed areas and areas from which dye has been removed.

Abrasion is generally followed by the third step, after-treatment that includes washing and rinsing steps during which detergents, optical brighteners, bleaching agents or softeners may be used. After the enzymatic treatment the reaction should be stopped in order to prevent damage of the treated materials, for example by temperature and/or pH inactivation, the latter comprising a thorough rinsing and/or detergent wash-off. This ensures that the mechanical strength of the fiber is not further compromised by the continued presence of the enzyme.

As used in the present context the expression "biostoning" of fabric or garment means the use of enzymes in place of, or in addition to, pumice stones for the treatment of fabric or garment, especially denim.

As stated above, treatment with cellulase can completely replace treatment with pumice stones. However, cellulase treatment can also be combined with pumice stone treatment, when it is desired to produce a heavily abraded finish.

Further, the endoglucanases are useful in biofinishing of fabrics and garments. "Biofinishing" (also called depilling, defuzzing, dehairing or biopolishing) refers to the use of enzymes in a controlled hydrolysis of cellulosic fibers in order to modify the fabric or yarn surface in a manner that permanently prevents tendency for pilling, improves fabric handle like softness and smoothness, clears the surface structure by reducing fuzzing, which results in clarification of colors and may also improve the drapability, moisture absorbency and the dyeability of the fabric.

Additional uses include the use in detergent compositions to improve fabric care properties by antipilling, antigraying, color clarification and softening, and to improve textile-cleaning effect, for instance soil removal.

Enzymatic depilling can be carried out at any stage during textile wet processing, preferably after optional desizing and/or bleaching, and similar conditions as in biostoning can be used. Also textiles in garment form can be treated.

The liquor ratio (the ratio of the volume of liquid per weight of fabric) in both biostoning and biofinishing may range from about 3:1 to 20:1, preferably 5:1 to 10:1. The treatment time can range between 15 min to 90 min and preferably 30 min to 60 min. It should be emphasized that the enzyme dosage greatly depends on the type of the fabrics, machinery, process conditions (pH, temperature, liquor ratio, treatment time, denim load, process scale) and type of enzyme preparation and like. A person skilled in art is capable in defining suitable dosages and conditions.

The process of the invention for treating cellulosic material also encompasses hydrolysis of lignocellulosic material for e.g. bioethanol production. One example of use of consolidated bioprocessing (CBP) in hydrolysis of lignocellulosic material is described e.g. by van Zyl et al. in Adv Biochem Eng Biotechnol. 2007; 108:205-35.

The invention is further illustrated by the following non-limiting examples.

Example 1

Screening for Strains Expressing Low-Temperature Cellulolytic Activity

About 180 fungal strains in the Roal Oy culture collection were tested for their ability to produce low-temperature cellulolytic activity. The fungal strains were cultivated in 100 ml volume on a rotary shaker (200 rpm) at temperature of 20° C. for 3-7 d. Several production media were tested containing Solka Floc cellulose as a carbon source. After the cultivation the cells and other solids were collected by centrifugation and the supernatant was recovered. If not used immediately, the preparation was stored in aliquots at −20° C.

For the estimation of the enzyme activity at lower temperatures, assays were performed of the shake flask cultivation preparation at 30° C. and 50° C. for 1 h. All shake flask supernatants were assayed for the following activities:

The endoglucanase (CMCase) activity:

This was assayed with 3% (w/v) carboxymethylcellulose (CMC) as the substrate in 50 mM citrate buffer essentially as described by Bailey and Nevalainen 1981; Haakana et al., 2004. Reducing sugars were measured with the DNS reagent. The assay was performed both at pH 5.0 and 7.0.

The endoglucanase (HEC) activity:

This was assayed with 1% (w/v) hydroxyethylcellulose (HEC) as the substrate in 50 mM citrate buffer essentially as described by Bailey and Nevalainen 1981. Reducing sugars were measured with the DNS reagent. The assay was performed both at pH 5.0 and 7.0.

Culture supernatant preparations of the strains were tested in small scale biostoning application in an LP-2 Launder Ometer as follows. About 7.2 g of desized denim swatches (12×12 cm) were loaded with steel balls into 1.2 liter containers containing 100 ml Mc Ilvaine's buffer and 100 ml culture supernatant, and the Launder Ometer was run at 30° C. for 120 min. After alkaline and detergent wash, the fabric samples were rinsed carefully with warm water and air dried. The results were evaluated both visually and by measuring the colour as reflectance values (data not shown).

After preliminary screening, four strains (*Geomyces pannorum* RF6293, RF6546 and RF6608, and *Fusarium* cf. *equiseti* RF6318) were chosen for additional application studies. For that purpose the strains RF6546 and RF6608 were cultivated in 200 ml volume on a rotary shaker (200 rpm) at a temperature of 20° C. for 4-7 d in a medium, which contains g/liter: Solka Floc cellulose 10.0, corn steep powder 1.5, soybean meal 0.5, CaCO$_3$ 0.5, (NH$_4$)$_2$HPO$_4$ 1.5, KH$_2$PO$_4$ 2.0, MgSO$_4$.H$_2$O 0.5, NaCl 0.5, NH$_4$NO$_3$ 0.5, Tween-80 0.5, trace element solution #1 0.5, trace element solution #2 0.5, paraffin oil 0.5; the pH was adjusted to 6.4. Trace element solution #1 (mg/liter): MnSO$_4$ 1.6, ZnSO$_4$.H$_2$O 3.45, CoCl$_2$.H$_2$O 2.0; Trace element solution #2 (mg/liter): FeSO$_4$.H$_2$O 5.0. The strains RF6293 and RF6318 were cultivated in 200 ml volume on a rotary shaker (200 rpm) at a temperature of 20° C. for 4-6 d in a medium, which contains g/liter: Solka Floc cellulose 30.0, corn steep powder 9.0, soybean meal 1.5, CaCO$_3$ 1.5, (NH$_4$)$_2$HPO$_4$ 4.5, KH$_2$PO$_4$ 6.0, MgSO$_4$.H$_2$O 1.5, NaCl 0.5, NH$_4$NO$_3$ 1.5, Tween-80 0.5, trace element solution #1 0.5, trace element solution #2 0.5, paraffin oil 0.5; the pH was adjusted to 6.4. Trace element solution #1 (mg/liter): MnSO$_4$ 1.6, ZnSO$_4$.H$_2$O 3.45, CoCl$_2$.H$_2$O 2.0; Trace element solution #2 (mg/liter): FeSO$_4$.H$_2$O 5.0.

Example 2

Cloning of the Endoglucanase Genes from *Geomyces pannorum* RF6293, RF6546, RF6608, and *Fusarium* cf. *equiseti* RF6318

Standard molecular biology methods were used in the isolation and enzyme treatments of DNA (plasmids, DNA fragments), in *E. coli* transformations, etc. The basic methods used are described in the standard molecular biology handbooks, e.g. Sambrook et al., (1989) and Sambrook and Russell (2001).

Lambda DASH®II/BamHI vector (Stratagene, USA) was used in the construction of the genomic libraries for *Geomyces pannorum* RF6293, RF6546, RF6608, and *Fusarium* cf. *equiseti* RF6318 according to the instructions from the supplier. The chromosomal DNAs, isolated by the method of Raeder and Broda (1985), were partially digested with Sau3A. The digested DNAs were size-fractionated and the fragments of the chosen size (5-20 kb) were ligated to the BamHI digested lambda vector arms. The ligation mixtures were packaged using Gigapack III Gold packaging extracts according to the manufacturer's instructions (Stratagene, USA). The titers of the constructed genomic libraries are presented in Table 1.

TABLE 1

Titers of the constructed genomic libraries

| Strain | Titer of the genomic library pfu/ml (×10$^6$) | Titer of the amplified genomic library pfu/ml (×10$^8$) |
|---|---|---|
| *Geomyces pannorum* RF6293 | 0.38 | 100.0 |
| *Geomyces pannorum* RF6546 | 0.04 | 6 |
| *Geomyces pannorum* R6608 | 0.04 | 0.3 |
| *Fusarium* cf. *equiseti* RF6318 | 0.46 | 60.0 |

The genomic libraries of *Geomyces pannorum* RF6293, RF6546, RF6608 and *Fusarium* cf. *equiseti* RF6318 were screened with the probes which were amplified by PCR using degenerate primers and the genomic DNA as a template. The sequences of the heterologous primers were based on the conserved endoglucanase sequences (Table 2, SEQ ID NO: 1-5). The conserved sequences were identified by aligning the previously published amino acid sequences of *Humicola grisea* var. *thermoidea* AB003107, *Fusarium oxysporum* L29381, *Melanocarpus albomyces* AJ515703 and *Gibberella zeae* AY342397. The PCR reaction mixtures contained 10 mM Tris-HCl, pH 8.8, 50 mM KCl, 0.1% Triton X-100, 1.5 mM MgCl$_2$, 0.1 mM dNTPs, 1 μM each primer and 1-2 units of Dynazyme II DNA polymerase (Finnzymes, Finland) and 0.5-1 μg of the genomic DNA. The conditions for the PCR reactions were the following: 5 min initial denaturation at 95° C., followed by 30 cycles of 1 min at 95° C., 30 s annealing at 52.5° C. (±7.5° C. gradient), 1 min extension at 72° C. and a final extension at 72° C. for 5 min. The genomic DNA templates used in the PCR reactions are listed in Table 3.

TABLE 2

The degenerate oligonucleotides tested as PCR primers to amplify probes for screening of endoglucanase genes from *Geomyces pannorum* RF6547, RF6546, RF6608, and *Fusarium* cf. *equiseti* RF6318

| Oligonucleotide | Length (bp) | Sequence[a] | SEQ ID NO. |
|---|---|---|---|
| Cel45_S1 | 20 | TAYTGGGAYTGYTGYAARCC (s) | 1 |
| Cel45_S2 | 17 | TGGTGYTGYGCNTGYTA (s) | 2 |
| Cel45_AS1 | 17 | TARCANGCRCARCACCA (as) | 3 |
| Cel45_AS2 | 17 | GTRCANCCRTCRAADAT (as) | 4 |
| Cel45_AS3 | 23 | TTRTCSGCRTTYTGRAACCARTC (as) | 5 |

[a]D = A or G or T, R = A or G, S = C or G, N = A or G or T or C, Y = T or C;
"s" in the parenthesis = sense strand,
"as" in the parenthesis = antisense strand.

DNA products having the expected sizes (estimated from the published endoglucanase sequences) were obtained from several reactions. The DNA fragments of the expected sizes were isolated from the most specific PCR reactions and they were cloned to pCR® 4-TOPO® vector (Invitrogen, USA). The inserts were characterized by sequencing and by performing Southern blot hybridizations to the genomic DNAs digested with several restriction enzymes. The PCR fragments, which were chosen to be used as probes for screening of the *Geomyces pannorum* RF6293, RF6546, RF6608, and *Fusarium* cf. *equiseti* RF6318 genomic libraries are presented in Table 3.

TABLE 3

The primers used in the PCR reactions and probes chosen for screening of the endoglucanase genes from *Geomyces pannorum* RF6293, RF6546, RF6608, and *Fusarium* cf. *equiseti* RF6318 genomic libraries. The genomic template DNA and the name of the plasmid containing the probe fragment are shown.

| Gene | Forward primer | Reverse primer | Genomic DNA used as a template in PCR reaction | Fragment obtained (kb) | SEQ ID NO | Insert in plasmid |
|---|---|---|---|---|---|---|
| RF6293_cel45A | Cel45_S1 | Cel45_AS3 | RF6293 | 0.6 kb | 6 | pALK2038 |
| RF6293_cel45B | Cel45_S1 | Cel45_AS3 | RF6289 | 0.6 kb | 7 | pALK2039 |
| RF6318_cel45A | Cel45_S1 | Cel45_AS3 | RF6318 | 0.6 kb | 8 | pALK2047 |
| RF6546_cel45A | Cel45_S1 | Cel45_AS3 | RF6546 | 0.6 kb | 9 | pALK2040 |
| RF6608_cel45A | Cel45_S1 | Cel45_AS3 | RF6608 | 0.6 kb | 10 | pALK2042 |
| RF6608_cel45B | Cel45_S1 | Cel45_AS3 | RF6608 | 0.6 kb | 11 | pALK2041 |

The deduced amino acid sequences from all these probes had homology to several published Cel45 sequences (BLAST program, version 2.2.9 at NCBI, National Center for Biotechnology Information; Altschul et al., 1990).

The inserts from the plasmids listed in Table 3 were labeled with digoxigenin according to the supplier's instructions (Roche, Germany). The amplified genomic libraries ($1 \times 10^5$-$6 \times 10^5$ plaques) were screened with labeled probe fragments. The hybridization temperature for the filters was 68° C. and the filters were washed 2×5 min at RT using 2×SSC-0.1% SDS followed by 2×15 min at 68° C. using 0.1×SSC-0.1% SDS. Several positive plaques were obtained from each of the hybridizations. Five strongly hybridizing plaques were purified from each screening. The phage DNAs were isolated and characterized by Southern blot hybridizations. The chosen restriction fragments hybridizing to the probe were subcloned to pBluescript II KS+ vector and the relevant regions of the clones were sequenced.

In total, six cel45 genes were cloned; one from *Geomyces pannorum* RF6546 and *Fusarium* cf. *equiseti* RF6318 strains, and two cel45 genes from *Geomyces pannorum* strains, RF6293 and RF6608. Table 4 summarizes the information on the probes used for screening the genes, the phage clones from which the genes were isolated, the chosen restriction fragments containing the full-length genes with their promoter and terminator regions, the plasmid names, and the DSM deposit numbers for the *E. coli* strains carrying these plasmids.

TABLE 4

The probes used for cloning of endoglucanase genes, the phage clone and the subclones chosen, the plasmid number and the number of the deposit of the corresponding *E. coli* strain

| Gene | Probe used in screening | Phage clone | The fragment subcloned to pBluescript II KS+ | Plasmid no | *E. coli* deposit no |
|---|---|---|---|---|---|
| Gp_RF6293_cel45A | pALK2038 | F78 | 3.5 kb HindIII | pALK2206 | DSM 18916 |
| Gp_RF6293_cel45B | pALK2039 | F105 | 2.3 kb XbaI | pALK2221 | DSM 19171 |
| Fe_RF6318_cel45A | pALK2047 | F122 | 2.5 kb EcoRI | pALK2226 | DSM 19173 |
| Gp_RF6546_cel45A | pALK2040 | F85 | 6.0 kb NotI | pALK2208 | DSM 18915 |
| Gp_RF6608_cel45A | pALK2042 | F88 | 2.5 kb XbaI | pALK2207 | DSM 18917 |
| Gp_RF6608_cel45B | pALK2041 | F108 | 9.0 kb XbaI | pALK2219 | DSM 19170 |

The relevant information on the genes and the deduced protein sequences (SEQ ID NO: 12-23) are summarized in Table 5 and Table 6, respectively.

TABLE 5

The summary on the endoglucanase genes isolated from *Geomyces pannorum* RF6293, RF6546, RF6608, and *Fusarium* cf. *equiseti* RF6318

| Gene | Length with introns (bp) [a] | Coding region (bp) [b] | No of introns | Lengths of introns (bp) | SEQ ID NO: |
|---|---|---|---|---|---|
| Gp_RF6293_cel45A | 1036 | 912 | 1 | 121 | 12 |
| Gp_RF6293_cel45B | 966 | 846 | 2 | 58, 59 | 14 |
| Fe_RF6318_cel45A | 1162 | 1098 | 1 | 61 | 16 |
| Gp_RF6546_cel45A | 1028 | 912 | 1 | 113 | 18 |
| Gp_RF6608_cel45A | 1026 | 912 | 1 | 111 | 20 |
| Gp_RF6608_cel45B | 969 | 846 | 2 | 61, 59 | 22 |

[a] The STOP codon is included.
[b] The STOP codon is not included.

TABLE 6

The summary of the amino acid sequences deduced from the endoglucanase gene sequences from *Geomyces pannorum* RF6293, RF6546, RF6608, and *Fusarium* cf. *equiseti* RF6318

| Endoglucanase protein | No of aas | Length of ss NN[a] | CBD[b] | Predicted MW (Da), ss not incl[c] | Predicted pI (ss not incl) | SEQ ID NO: |
|---|---|---|---|---|---|---|
| Gp_RF6293_Cel45A | 304 | 22 | T247 to L282 | 28678 | 5.13 | 13 |
| Gp_RF6293_Cel45B | 282 | 26 | | 27309 | 4.17 | 15 |
| Fe_RF6318_Cel45A | 366 | 20 | A306 to N346 | 36284 | 8.25 | 17 |
| Gp_RF6546_Cel45A | 304 | 22 | T247 to L282 | 28762 | 4.93 | 19 |
| Gp_RF6608_Cel45A | 304 | 22 | T247 to L282 | 28504 | 4.33 | 21 |
| Gp_RF6608_Cel45B | 282 | 26 | | 30324 | 4.37 | 23 |

[a]The prediction on the signal sequence was made using the program SignalP V3.0 (Nielsen et al., 1997; Bendtsen et al., 2004); the NN value was obtained using neural networks.
[b]The cellulose-binding domain (CBD), the amino acids of the CBD region are indicated [M1(Met #1) included in numbering].
[c]The predicted signal sequence was not included. The prediction was made using the Compute pI/MW tool at ExPASy server (Gasteiger et al., 2003).

The comparisons of the deduced Cel45 sequences from *Geomyces pannorum* RF6293, RF6546, RF6608, and *Fusarium* cf. *equiseti* RF6318 strains to each other are presented in Table 7 and Table 8. Both the full-length amino acid sequences and the core proteins without the CBD region of the deduced Cel45 sequences are shown. A programme of Clone Manager (version 9) including the functions "Compare Two Sequences/Global/Compare sequences as amino acids/BLOSUM62 scoring matrix" was used for determining the degree of identity.

TABLE 7

The identity values (%) obtained from alignment of the deduced Cel45 amino acid sequences from *Geomyces pannorum* RF6293, RF6546 and RF6608, and *Fusarium* cf. *equiseti* RF6318. The full-length amino acid sequences including the signal sequences were aligned.

| Protein | Gp_RF6293 Cel45A | Gp_RF6293 Cel45B | Fe_RF6318 Cel45A | Gp_RF6546 Cel45A | Gp_RF6608 Cel45A | Gp_RF6608 Cel45B |
|---|---|---|---|---|---|---|
| Gp_RF6293_Cel45A | 100 | 39 | 46 | 85 | 87 | 38 |
| Gp_RF6293_Cel45B | | 100 | 30 | 40 | 38 | 89 |
| Fe_RF6318_Cel45A | | | 100 | 45 | 45 | 31 |
| Gp_RF6546_Cel45A | | | | 100 | 87 | 38 |
| Gp_RF6608_Cel45A | | | | | 100 | 38 |
| Gp_RF6608_Cel45B | | | | | | 100 |

TABLE 8

The identity values (%) obtained from alignment of the deduced Cel45 amino acid sequences from *Geomyces pannorum* RF6293, RF6546, RF6608, and *Fusarium* cf. *equiseti* RF6318. The core sequences excluding the signal sequence and linker-CBD regions were aligned.

| Protein | Gp_RF6293 Cel45A | Gp_RF6293 Cel45B | Fe_RF6318 Cel45A | Gp_RF6546 Cel45A | Gp_RF6608 Cel45A | Gp_RF6608 Cel45B |
|---|---|---|---|---|---|---|
| Gp_RF6293_Cel45A | 100 | 41 | 58 | 88 | 89 | 41 |
| Gp_RF6293_Cel45B | | 100 | 39 | 42 | 42 | 89 |
| Fe_RF6318_Cel45A | | | 100 | 60 | 60 | 39 |
| Gp_RF6546_Cel45A | | | | 100 | 92 | 42 |
| Gp_RF6608_Cel45A | | | | | 100 | 41 |
| Gp_RF6608_Cel45B | | | | | | 100 |

Comparison of the deduced Cel45 endoglucanase sequences from *Geomyces pannorum* RF6293, RF6546, RF6608, and *Fusarium* cf. *equiseti* RF6318 to sequences found in databases are shown in Tables 9A and 9B.

TABLE 9A

The highest identity sequences to the deduced endoglucanase sequences of the *Geomyces pannorum* RF6293, RF6546, RF6608, and *Fusarium* cf. *equiseti* RF6318.

| Organism and accession number | Identity (%) |
| --- | --- |
| Gp_RF6293_Cel45A | 100 |
| *Neurospora crassa*, XM_952014 | 57 |
| Gp_RF6293_Cel45B | 100 |
| *Pyrenophora tritici-repentis*, XM_001935986 | 47 |
| Fe_RF6318_Cel45A | 100 |
| *Gibberella zeae*, AY342397 | 86 |
| *Gibberella zeae*, XM_382834 | 86 |
| Gp_RF6546_Cel45A | 100 |
| *Neurospora crassa*, XM_952014 | 57 |
| Gp_RF6608_Cel45A | 100 |
| *Sclerotinia sclerotiorum*, XM_001597582 | 58 |
| Gp_RF6608_Cel45B | 100 |
| *Pyrenophora tritici-repentis*, XM_001935986 | 48 |

The full-length amino acid sequences including the signal sequences were aligned. The database search was performed using BLAST (tblastn, nr/nt database), and Clone Manager 9 programme (Compare Two Sequences/Global/Compare sequences as amino acids/BLOSUM62 scoring matrix) was used for determining the degree of identity.

TABLE 9B

The highest identity of patent publication sequences to the deduced endoglucanase sequences of the *Geomyces pannorum* RF6293, RF6546, and *Fusarium* cf. *equiseti* RF6318.

| Organism and accession number | Identity (%) |
| --- | --- |
| Gp_RF6293_Cel45A | 100 |
| U.S. Pat. No. 7,256,032, SEQ ID: 21 | 64 |
| Fe_RF6318_Cel45A | 100 |
| U.S. Pat. No. 5,610,129 A, SEQ ID: 4 | 78 |
| Gp_RF6546_Cel45A | 100 |
| US2005070003A1, SEQ ID: 6 | 61 |

The full-length amino acid sequences including the signal sequences were aligned. The Chemical Abstracts Service (CAS) Registry System, DGEGE and Patended Protein Sequences NCBI database searches were performed using BLAST, and Clone Manager 9 programme (Compare Two Sequences/Global/Compare sequences as amino acids/BLOSUM62 scoring matrix) was used for determining the degree of identity.

Example 3

Production of Recombinant Cel45 Proteins in *Trichoderma reesei*

Expression plasmids were constructed for overexpression of recombinant Cel45 proteins from *Geomyces pannorum* RF6293 and RF6546, and *Fusarium* cf. *equiseti* RF6318 in *Trichoderma reesei*. The expression plasmids constructed are listed in Table 10. The recombinant cel45 genes, including their own signal sequences, were exactly fused to the *T. reesei* cbh1/cel7A promoter (p cbh1). The transcription termination was ensured by the *T. reesei* cbh1/cel7A terminator (t cbh1) and the *A. nidulans* amdS marker gene was used for selection of the transformants as described in Paloheimo et al. (2003). The linear expression cassettes (FIG. 1) were isolated from the vector backbones after NotI digestion and were transformed into *T. reesei* A47 and/or A51 protoplasts (both strains has the genes encoding the four major cellulases CBHI/Cel7A, CBHII/Cel6A, EGI/Cel7B and EGII/Cel5A deleted). The transformations were performed as in Penttilä et al. (1987) with the modifications described in Karhunen et al. (1993), selecting acetamide as a sole nitrogen source (amdS marker gene). The transformants were purified on selection plates through single conidia prior to sporulating them on PD.

TABLE 10

The expression cassettes constructed to overproduce Cel45 proteins from *Geomyces pannorum* RF6293 and RF6546, and *Fusarium* cf. *equiseti* RF6318 in *Trichoderma reesei*.

| Endoglucanase protein | Expression Plasmid | Expression cassette [a] | Terminator [b] |
| --- | --- | --- | --- |
| Gp_RF6293_Cel45A | pALK2215 | 8.6 kb NotI | 196 bp (MlyI) |
| Gp_RF6293_Cel45B | pALK2224 | 8.6 kb NotI | 196 bp (SalI) |
| Fe_RF6318_Cel45A | pALK2230 | 8.9 kb NotI | 335 bp (EcoRI) |
| Gp_RF6546_Cel45A | pALK2218 | 8.6 kb NotI | 225 bp (SspI) |

The overall structure of the expression cassettes was as described in FIG. 1. The cloned cel45 genes were exactly fused to the *T. reesei* cbh1/cel7A promoter.
[a] The expression cassette for *T. reesei* transformation was isolated from the vector backbone by using NotI digestion.
[b] The number of the nucleotides after the STOP codon of the cloned recombinant gene that was included in the expression cassette. The restriction site at the 3'-end of the genomic gene fragment that was used in the construction of the expression cassette is indicated in parenthesis.

The endoglucanase production of the transformants was analysed from the culture supernatants of the shake flask cultivations (50 ml). The transformants were grown for 7 days in a complex lactose-based cellulase-inducing medium (Joutsjoki et al. 1993) buffered with 5% $KH_2PO_4$. The endoglucanase activity was assayed with 3% (w/v) carboxymethylcellulose (CMC) as the substrate in 50 mM citrate buffer according to Bailey and Nevalainen 1981 and Haakana et al., 2004. The genotypes of the chosen transformants were confirmed by using Southern blots in which several genomic digests were included and the respective expression cassette was used as a probe. Heterologous production of recombinant endoglunase proteins was analyzed by SDS-PAGE with subsequent Coomassive staining.

Figure 2:
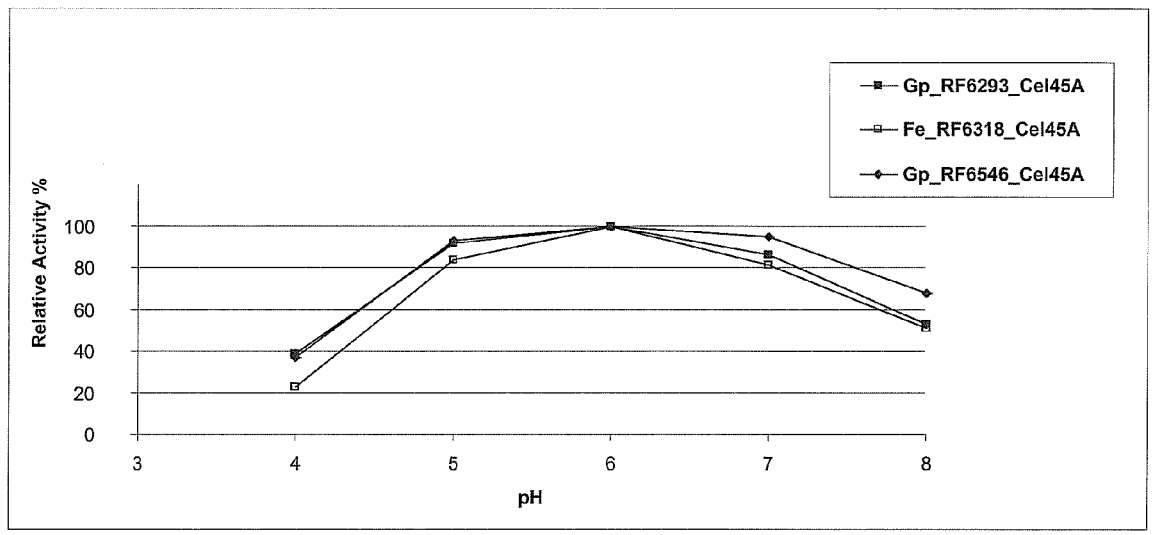
FIG. 2A shows pH optima of the recombinant Cel45A protein preparations, and 2B shows the thermal stability of recombinant Cel45A protein preparations.
Figure 2:
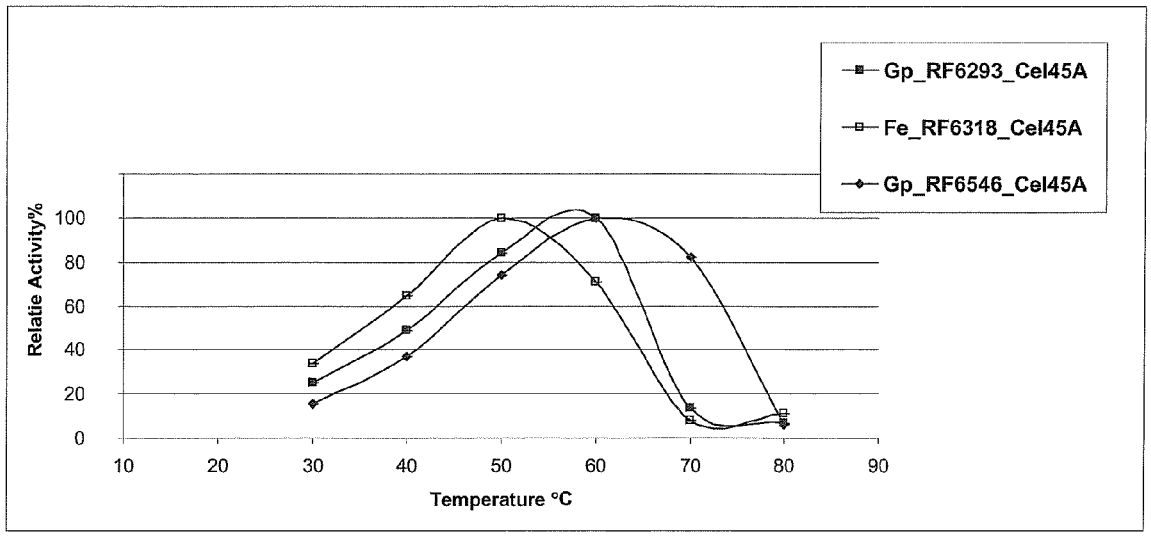

The recombinant Cel45A enzyme preparations were characterized in terms of pH optimum and thermal stability. The pH optima of the overproduced Cel45A proteins were determined in universal McIlvaine buffer within a pH range of 4.0-8.0 using 3% (w/v) carboxymethylcellulose (CMC) as substrate (FIG. 2A). Thermal stability of the recombinant endoglucanase proteins was determined by measuring the CMCase activity in universal McIlvaine buffer at the optimum pH with a reaction time of 1 h (FIG. 2B).

The chosen endoglucanase producing transformants were cultivated in lab bioreactors at 28° C. in the medium indicated above for 3-4 days with pH control 4.4±0.2 ($NH_3/H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany).

Example 4

Performance of Recombinant Cel45 Proteins in Denim Treatment at Different Temperatures Recombinant Cel45 proteins produced as described in Example 3 using *Trichoderma* as host were tested for their effect in biostoning of denim at different temperatures to create an abraded look similar to that provided by pumice stones. Commercial Cel45 enzymes Ecostone®N400 (Roal Oy, Finland) and Denimax™ 399S (Novozymes) were used for comparison.

One pair of jeans made of Indigo dyed denim twill obtained from an English supplier was used as main test material after desizing with ECOSTONE® A200 alpha-amylase and 2 pairs of desized Apache jeans (Labels Fashion Limited, U.K.) as filler material. The cellulase treatments were performed with Electrolux's Wascator FOM 71 CLS washer extractor under conditions described in Table 11.

TABLE 11

The test conditions/process parameters used in cellulase treatments

| Process parameter | |
|---|---|
| Denim load | 1.6 kg |
| Water | 17 liter |
| Buffer/pH control (pH 6) | Adjusted with $Na_2HPO_4\ H_2O$ and citric acid |
| Time | 55 min |
| Temperature | 20, 30, 40, 50 or 60° C. |
| Cellulase dosage | 250-1500 NCU/g fabric |

The enzymes were dosed as neutral cellulase activity units (NCU) per weight of fabric. The enzyme activity was measured as the release of reducing sugars from carboxymethylcellulose (3% CMC) at 50° C. in 50 mM Hepes buffer pH 7.0 (NCU activity Haakana et al. 2004). Recombinant Cel45 proteins were dosed as 1250 NCU/g fabric, Ecostone®N400 1500 NCUIg fabric and Denimax™ 399S 250 NCU/g. Dosing of each enzyme was sufficient to give easily measurable/detectable differences (increase of lightness=delta L*>2 units) at the whole temperature range. Enzymes were inactivated after draining by raising the pH above 11 by adding 4.2 g of NaOH (10 min, 40° C.) and rinsing three times. The jeans were dried in a tumbler.

The biostoning effect/abrasion level of the main test material was evaluated by measuring the colour as reflectance values with Minolta CM 2500 spectrophotometer using L*a*b* colour space coordinates (illuminant D65/2°). The colour from the face side and the reverse side of the denim was measured after desizing (i.e. before cellulase treatment) and after the cellulase treatment. Each measurement on the face side of denim was the average of approximate 40 measurements. Temperature profiles in denim application were also illustrated by calculating the relative performance (%) at 30° C. compared to 50° C. (30:50 ratio) and relative performance (%) at 40° C. compared to optimal temperature (40/OT ratio). The results are shown in Tables 12-14 and FIG. 3.

TABLE 12

Temperature profiles of Cel45 preparations in denim treatment.

| Enzyme | Temp. (° C.) | Relative increase of L* (%) |
|---|---|---|
| Gp_RF6293_Cel45A | 60 | 54 |
| Gp_RF6293_Cel45A | 50 | 95 |
| Gp_RF6293_Cel45A | 40 | 100 |
| Gp_RF6293_Cel45A | 30 | 93 |
| Gp_RF6293_Cel45A | 20 | 65 |
| Gp_RF6546_Cel45A | 60 | 99 |
| Gp_RF6546_Cel45A | 50 | 100 |
| Gp_RF6546_Cel45A | 40 | 81 |
| Gp_RF6546_Cel45A | 30 | 74 |
| Fe_RF6318_Cel45A | 50 | 96 |
| Fe_RF6318_Cel45A | 40 | 100 |
| Fe_RF6318_Cel45A | 30 | 76 |
| Fe_RF6318_Cel45A | 20 | 62 |
| Ecostone ® N400 | 60 | 100 |
| Ecostone ® N400 | 50 | 91 |
| Ecostone ® N400 | 40 | 75 |
| Ecostone ® N400 | 30 | 64 |
| Denimax ™ 399S | 60 | 100 |
| Denimax ™ 399S | 50 | 92 |
| Denimax ™ 399S | 40 | 62 |
| Denimax ™ 399S | 30 | 40 |

Treatments with commercial Cel45 enzyme preparations were used for comparison.

TABLE 13

30:50 and 40:OT ratios calculated from temperature profiles of novel Cel45 enzymes and commercial Cel45 preparations

| Enzyme | 30:50 ratio (%) | 40:OT ratio (%) |
|---|---|---|
| Gp_RF6293_Cel45A | 98 | 100 |
| Gp_RF6546_Cel45A | 74 | 81 |
| Fe_RF6318_Cel45A | 79 | 100 |
| Ecostone ® N400 | 70 | 75 |
| Denimax ™ 399S | 43 | 62 |

Figure 3:
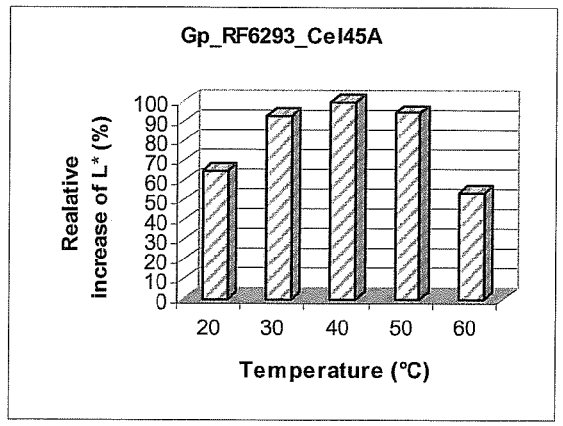
FIG. 3A-E shows temperature profiles of novel Cel45 preparations compared to commercial Cel45 preparations in denim treatment.
Figure 3:
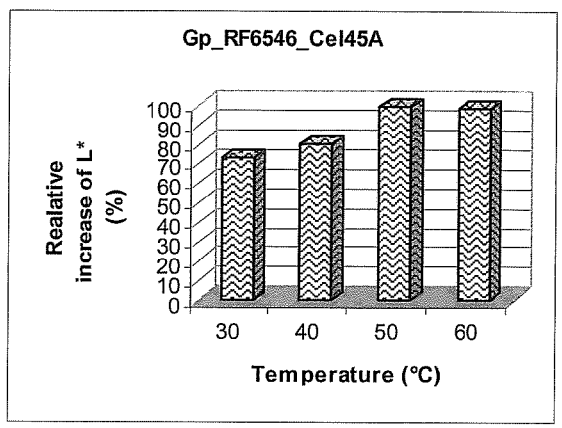
Figure 3:
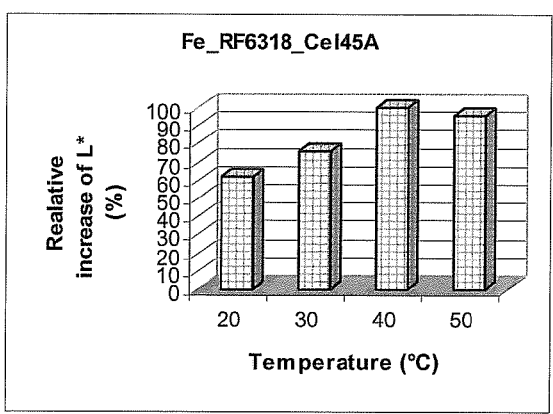
Figure 3:
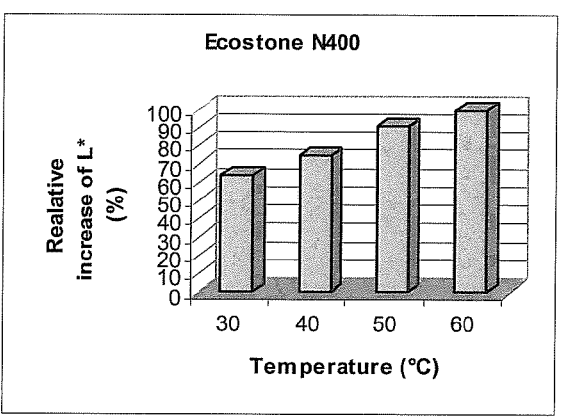
Figure 3:
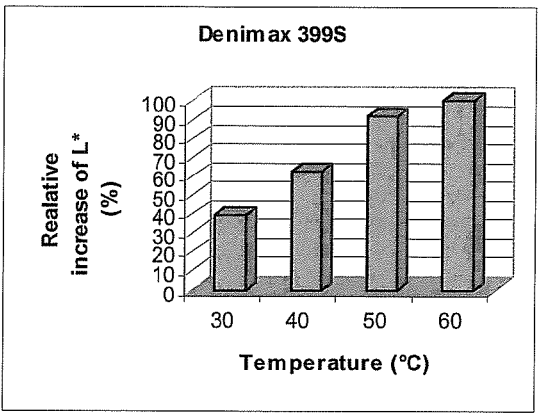

The results in Table 12 and FIG. 3 show that the novel recombinant Cel45 enzymes have lower temperature profiles in application than the commercial Cel45 enzymes Ecostone®N400 and Denimax™ 399S. Gp_RF6293_Cel45A shows optimal performance at a very broad temperature range from 30 to 50° C., which is surprising, because the temperature optimum at analytical conditions was remarkably higher (55-60° C., FIG. 2B). The optimal temperature range for Gp_RF6546_Cel45A and Fe_RF6318_Cel45A is also lower than for the commercial enzymes.

Both Gp_RF6293_Cel45A and Fe_RF6318_Cel45A have higher performance at 40° C. than at 50° C., which is a unique property compared to other enzymes belonging to the cel45 family, like the commercial preparations used as reference, and which typically work best at 50-60° C. The results in Table 13 show that both 30/50 and 40/OT ratios are more favorable with these novel endoglucanases than with commercial Cel45 preparations.

The results in Table 14 show that with the recombinant Gp_RF6293_Cel45A enzyme a higher biostoning/abrasion effect at low temperature (30° C.) can be obtained compared to commercial Cel45 enzymes.

TABLE 14

Colour measurements of the face side of denim treated with Gp_RF6293_Cel45A preparation at 30° C. and pH 6.

| Enzyme | Activity/ g garment | Before cellulase treatment L* | After cellulase treatment L* | Increase of L* |
|---|---|---|---|---|
| Gp_RF6293_Cel45A | 1250 NCU/g | 16.87 | 22.19 | 5.32 |
| Ecostone ® N400 | 1500 NCU/g | 16.95 | 21.75 | 4.80 |
| Denimax ™ 399S | 250 NCU/g | 16.82 | 19.29 | 2.47 |
| Denimax ™ 399S | 1250 NCU/g | 16.82 | 21.36 | 4.54 |

Treatments with commercial enzyme preparations were used for comparison. L* indicates the lightness.

Example 5

Performance of Recombinant Cel45 Proteins in Denim Treatment at Different pH Recombinant Cel45 proteins produced as described in Example 3 using *Trichoderma* as host were tested for their effect in biostoning of denim at different pH to create an abraded look similar to that provided by pumice stones.

The test system for biostoning was as in Example 4, except that a different batch of jeans was used and the temperature was 40° C. and pH 5-7. Also the effect of the cellulase treatment was evaluated as in Example 4.

Figure 4A:
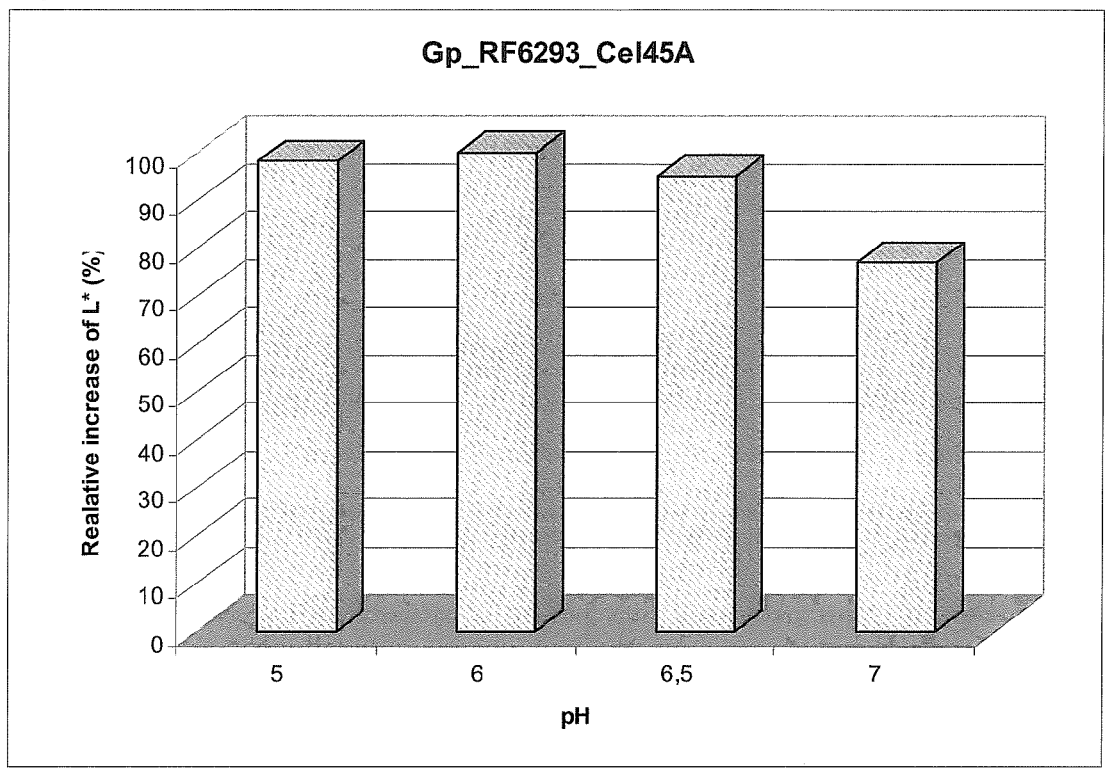
FIG. 4A-B shows the performance of novel Cel45 preparations at different pH in denim treatment.
Figure 4B:
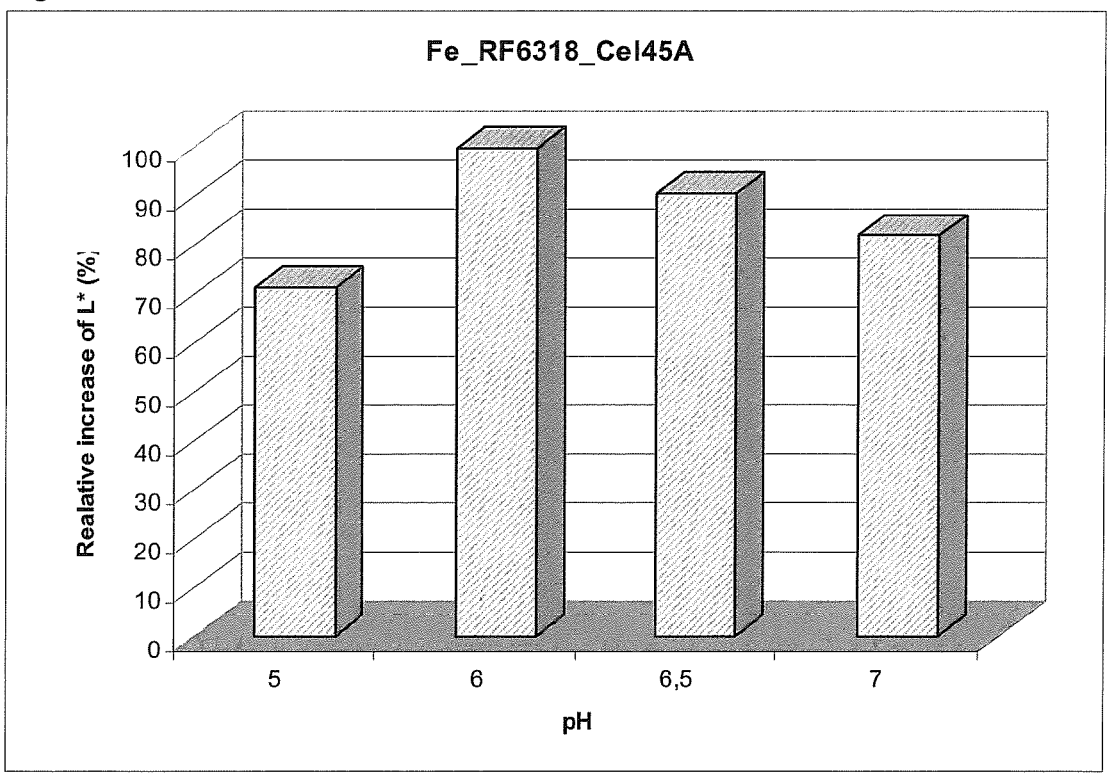
Figure 5:
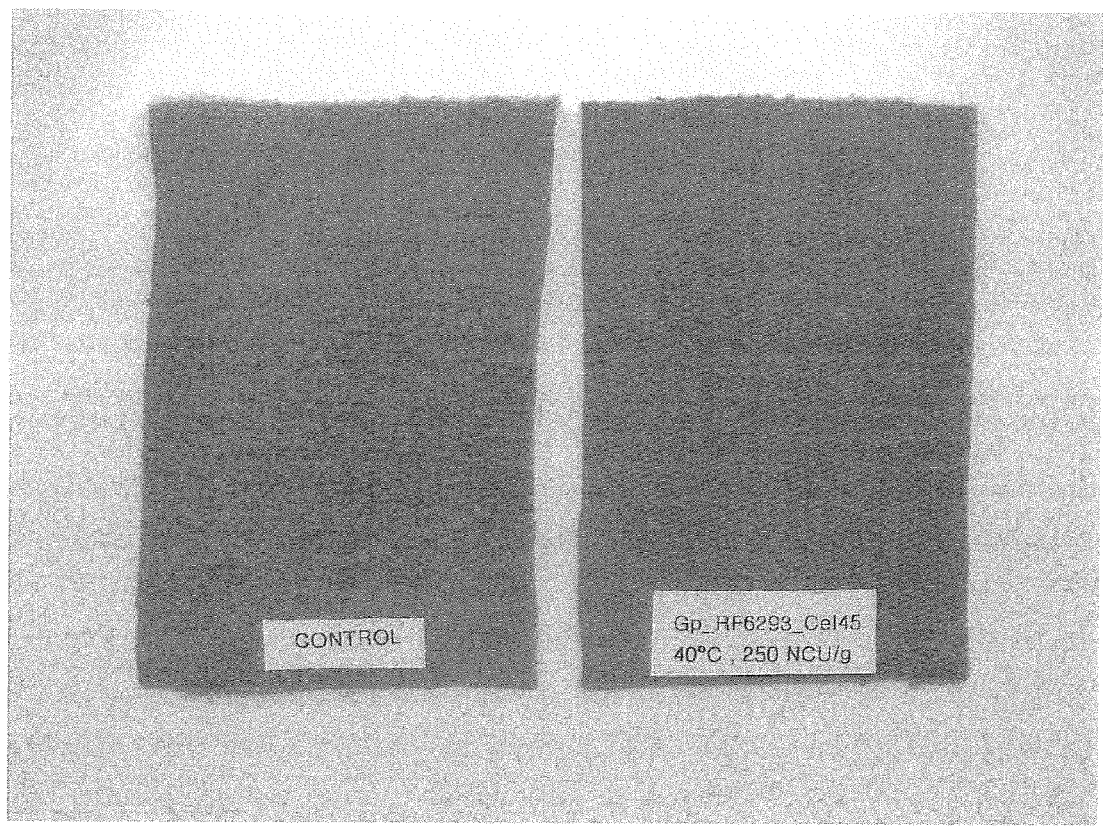
FIG. 5 shows the performance of Gp_RF6293_Cel45 in biofinishing (defuzzing) treatment at 40° C. compared to control sample without enzyme.

The results are set forth in Table 15 and FIG. 4, which show that the optimal pH range for Gp_RF6293_Cel45A is 5-6.5 and for Fe_RF6318_Cel45A 6-6.5.

TABLE 15

Colour measurements of the face side of denim treated with recombinant Cel45 preparations at different pH at 40° C.

| Enzyme | pH | Before cellulase treatment L* | After cellulase treatment L* | Increase of L* |
|---|---|---|---|---|
| Gp_RF6293_Cel45A | 5 | 16.70 | 22.33 | 5.63 |
| Gp_RF6293_Cel45A | 6 | 16.63 | 22.36 | 5.73 |
| Gp_RF6293_Cel45A | 6.5 | 16.75 | 22.2 | 5.45 |
| Gp_RF6293_Cel45A | 7 | 16.75 | 21.16 | 4.41 |
| Fe_RF6318_Cel45A | 5 | 16.55 | 19.5 | 2.95 |
| Fe_RF6318_Cel45A | 6 | 16.53 | 20.66 | 4.13 |
| Fe_RF6318_Cel45A | 6.5 | 16.47 | 20.22 | 3.75 |
| Fe_RF6318_Cel45A | 7 | 16.53 | 19.92 | 3.39 |

L* indicates the lightness.

Example 6

Performance of Recombinant Cel45 Proteins in Biofinishing (Depilling/Dehairing/Defuzzing)

The ability of recombinant Cel45 proteins produced as described in Example 3 using *Trichoderma* as host were tested in depilling of cotton knitwear and compared to Cel45 enzyme with excellent depilling properties (WO2006/117432). The cellulase treatments were performed with Electrolux's Wascator FOM 71 CLS washer extractor under conditions described in Table 16.

Three yarn fleece made of 100% cotton (Type 9761, Orneule, Finland) was used as test material with filling material. Fabric was first prewashed for 10 min at 50° C. and rinsed 3 times. After that the cotton knit fabric was treated with cellulase at 40° C. or 50° C. for 60 minutes. Enzymes were dosed as neutral cellulase activity units (NCU) per the weight of the fabric. After draining the enzyme was inactivated (for 10 min at 60° C.) by raising the pH above 11 with sodium hydroxide. The fabric was then rinsed three times and dried in a tumbler.

TABLE 16

The test conditions/process parameters used in biofinishing treatments

| Process parameter | |
|---|---|
| Fabric load | 1.0 kg |
| Water | 15 liter |
| pH adjustment | With acetic acid (80%) |
| Time | 60 min |
| Temperature | 40° C./50° C. |
| Cellulase dosage | 250 NCU/g fabric |

The knitwear samples were evaluated visually according to how much surface fibrils and fuzz was detected. The result of each evaluation was quantified by indicating the result relative to a scale consisting of standards. These standards were pieces of the same fabric washed with different amounts of cellulase and they had a range of intensity of surface fibrils/fuzz from 1 to 5 with half unit's intervals. Number 0 was a control sample treated without enzyme. The higher the number, the better the depilling/dehairing effect is. Number 5 means that the surface fibrils/fuzz were/was removed. The results are shown in Tables 17 and 18. The results in Tables 17 and 18 show that Gp_RF6293_Cel45A, Gp_RF6546_Cel45A and Fe_RF6318_Cel45A have excellent depilling properties. It was surprising that Gp_RF6293_Cel45A was efficient in much lower activity dosage in depilling/dehairing than in denim treatment in the previous Examples. It was also found that the most optimal pH range for Gp_RF6293_Cel45A in depilling is from 5.5 to ca. 7.

A neutral cellulase having excellent depilling properties, like the Gp_RF6293_Cel45A protein, enables biofinishing treatment simultaneously with dyeing.

TABLE 17

The results of biofinishing treatments with recombinant Cel45 proteins at 40° C. and pH 6

| Enzyme | Activity/g fabric | Evaluation |
|---|---|---|
| Cel45 (WO2006/117432) | 250 NCU/g | 3.5 |
| Gp_RF6293_Cel45A | 500 NCU/g | 5 |
| Gp_RF6293_Cel45A | 250 NCU/g | 4 |
| Gp_RF6293_Cel45A | 125 NCU/g | 3 |

4-5 means excellent depilling/defuzzing effect, 3 good depilling/defuzzing effect, 0 no depilling/defuzzing effect (treatment without enzyme).

TABLE 18

The results of biofinishing treatments with recombinant Cel45 proteins at 50° C. and pH 6

| Enzyme | g fabric | Conditions | Evaluation |
|---|---|---|---|
| Control | 0 | pH 6, 50° C. | 0 |
| Gp_RF6293_Cel45A | 500 NCU/g | pH 6, 50° C. | 5 |
| Gp_RF6546_Cel45A | 1000 NCU/g | pH 6, 50° C. | 4 |
| Fe_RF6318_Cel45A | 1250 NCU/g | pH 6, 50° C. | 5 |
| Fe_RF6318_Cel45A | 625 NCU/g | pH 6, 50° C. | 4.5 |

REFERENCES

Altschul S F, W Gish, W Miller, E W Myers and D J Lipman. 1990. Basic local alignment search tool. J. Mol. Biol. 215: 403.410.

Bailey M and Nevalainen H. 1981. Induction, isolation and testing of stable *Trichoderma reesei* mutants with improved production of solubilizing cellulase. Enzyme Microb. Technol. 3:153-157.

Bendtsen J D, H Nielsen, G von Heijne and S Brunak. 2004. Improved prediction of signal peptides: SignalP 3.0. J. Mol. Biol. 340:783-795.

Gasteiger E, A Gattiker, C Hoogland, I Ivanyi, R D Appel and A Bairoch. 2003. ExPASy: the proteiomics server for in-depth protein knowledge and analysis. Nucleic Acids Res. 31:3784-3788.

Haakana H, Miettinen-Oinonen A, Joutsjoki V, Mäntylä A, Suominen P and Vehmaanperä J. 2004. Cloning of cellulase genes from *Melanocarpus albomyces* and their efficient expression in *Trichoderma reesei*. Enzyme Microb. Technol. 34:159-167.

Henrissat B. (1991) A classification of glycosyl hydrolases based on amino acid sequence similarities. Biochem. J. 280: 309-316.

Henrissat B. and Bairoch A. (1993) New families in the classification of glycosyl hydrolases based on amino acid sequence similarities. Biochem. J. 293: 781-788.

Henrissat B. and Bairoch A. (1996). Updating the sequence-based classification of glycosyl hydrolases. Biochem. J. 316: 695-696.

Joutsjoki, V V, T K Torkkeli and K M H Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Karhunen T, A Mäntylä, K M H Nevalainen and P L Suominen. 1993. High frequency one-step gene replacement in *Trichoderma reesei*. I. Endoglucanase I overproduction. Mol. Gen. Genet. 241:515-522.

Malardier L, Daboussi M J, Julien J, Roussel F, Scazzocchio C and Brygoo Y. 1989. Cloning of the nitrate reductase gene (niaD) of *Aspergillus nidulans* and its use for transformation of *Fusarium oxysporum*. Gene 15:147-156.

Needleman S, and Wunsch C. (1970) A general method applicable to the search for similarities in the amino acid sequence of two proteins. Journal of Molecular Biology 48, 443-453.

Nielsen H, J Engelbrecht, S Brunak and G von Heijne. 1997. Identification of prokaryotic and eykaryotic signal peptides and prediction of thier cleavage sites. Protein Engineering 10:1-6.

Nierstrasz V. A. and Warmoeskerken M. M. C. G. (2003) Process engineering and industrial enzyme applications. In: Textile processing with enzymes. A. Cavaco-Paulo and G. M. GUbitz (eds.) Woodhead Publishing Ltd, Cambridge. pp. 120-157.

Rice P, Longden I and Bleasby A. (2000). EMBOSS: The European Molecular Biology Open Software Suite. Trends in Genetics 16:276-277.

Paloheimo M, A Mäntylä, J Kalilo, and P Suominen. 2003. Highyield production of a bacterial xylanase in the filamentous fungus *Trichoderma reesei* requires a carrier polypeptide with an intact domain structure. Appl. Env. Microbiol. 69:7073-7082.

Penttilä M, H Nevalainen, M Ratto, E Salminen and J Knowles. 1987. A versatile transformation system for the cellulolytic filamentous fungus *Trichoderma reesei*. Gene 61:155-164.

Raeder U and P Broda. 1985. Rapid preparation of DNA from filamentous fungi. Lett. Appl. Microbiol. 1:17-20.

Sambrook J, E F Fritsch and T Maniatis. 1989. Molecular cloning, a laboratory manual. Cold Spring Harbor Laboratory, New York, US.

Sambrook J and DW Russell. 2001. Molecular cloning, a laboratory manual. Cold Spring Harbor Laboratory, New York, US.

van Zyl W H, Lynd L R, den Haan R, McBride J E. 2007 Consolidated bioprocessing for bioethanol production using *Saccharomyces cerevisiae*. Adv Biochem Eng Biotechnol.; 108:205-35.

Sequences

| SEQ ID NO: | Sequence |
|---|---|
| 1 | Oligonucleotide primer Cel45_S1 |
| 2 | Oligonucleotide primer Cel45_S2 |
| 3 | Oligonucleotide primer Cel45_AS1 |
| 4 | Oligonucleotide primer Cel45_AS2 |
| 5 | Oligonucleotide primer Cel45_AS3 |
| 6 | PCR fragment obtained from *G. pannorum* RF6293 using the primers Cel45_S1 and Cel45_AS3 |
| 7 | PCR fragment obtained from *G. pannorum* RF6289 using the primers Cel45_S1 and Cel45_AS3 |
| 8 | PCR fragment obtained from *F.* cf. *equiseti* RF6318 using the primers Cel45_S1 and Cel45_AS3 |
| 9 | PCR fragment obtained from *F.* cf. *equiseti* RF6546 using the primers Cel45_S1 and Cel45_AS3 |
| 10 | PCR fragment obtained from *G. pannorum* RF6608 using the primers Cel45_S1 and Cel45_AS3 |
| 11 | PCR fragment obtained from *G. pannorum* RF6608 using the primers Cel45_S1 and Cel45_AS3 |
| 12 | Nucleotide sequence of the *G. pannorum* RF6293 cel45A gene |
| 13 | Deduced amino acid sequence of the *G. pannorum* RF6293 Cel45A |
| 14 | Nucleotide sequence of the *G. pannorum* RF6293 cel45B gene |
| 15 | Deduced amino acid sequence of the *G. pannorum* RF6293 Cel45B |
| 16 | Nucleotide sequence of the *F.* cf. *equiseti* RF6318 cel45A gene |
| 17 | Deduced amino acid sequence of the *F.* cf. *equiseti* RF6318 Cel45A |
| 18 | Nucleotide sequence of the *G. pannorum* RF6546 cel45A gene |
| 19 | Deduced amino acid sequence of the *G. pannorum* RF6546 Cel45A |
| 20 | Nucleotide sequence of the *G. pannorum* RF6608 cel45A gene |

-continued

| SEQ ID NO: | Sequence |
|---|---|
| 21 | Deduced amino acid sequence of the *G. pannorum* RF6608 Cel45A |
| 22 | Nucleotide sequence of the *G. pannorum* RF6608 cel45B gene |
| 23 | Deduced amino acid sequence of the *G. pannorum* RF6608 Cel45B |

Deposited Microorganisms

| Deposited strain | Culture collection | Deposition date | Accession number |
|---|---|---|---|
| *Geomyces pannorum* RF6293 | 1) | 7 Apr. 2006 | CBS 119567 |
| *Fusarium* cf. *equiseti* RF6318 | 1) | 7 Apr. 2006 | CBS 119568 |
| *Geomyces pannorum* RF6546 | 1) | 16 Jun. 2006 | CBS 119958 |
| *Geomyces pannorum* RF6608 | 1) | 16 Jun. 2006 | CBS 119962 |
| *E. coli* strain including the plasmid pALK2206 | 2) | 10 Jan. 2007 | DSM 18916 |
| *E. coli* strain including the plasmid pALK2221 | 2) | 16 Mar. 2007 | DSM 19171 |
| *E. coli* strain including the plasmid pALK2226 | 2) | 16 Mar. 2007 | DSM 19173 |
| *E. coli* strain including the plasmid pALK2208 | 2) | 10 Jan. 2007 | DSM 18915 |
| *E. coli* strain including the plasmid pALK2207 | 2) | 10 Jan. 2007 | DSM 18917 |
| *E. coli* strain including the plasmid pALK2219 | 2) | 16 Mar. 2007 | DSM 19170 |

1) Centraalbureau Voor Schimmelcultures at Upsalalaan 8, 3508 AD, Utrecht, the Netherlands
2) Deutsche Sammlung von Mikroorganismen und Zellkulturen GmbH (DSMZ), Inhoffenstrasse 7B, D-38124 Braunschweig, Germany

The invention claimed is:

1. An isolated fungal endoglucanase polypeptide, which belongs to glycosyl hydrolase family 45, which shows substantial performance at low temperatures, and which comprises an amino acid sequence having at least 90% sequence identity to SEQ ID NO: 13, 15, 17, 19, 21 or 23.

2. The endoglucanase polypeptide of claim 1, which comprises an amino acid sequence having at least 95% sequence identity to SEQ ID NO: 13, 15, 17, 19, 21 or 23.

3. The endoglucanase polypeptide of claim 1, which comprises an amino acid sequence having at least 98% sequence identity to SEQ ID NO: 13, 15, 17, 19, 21 or 23.

4. The endoglucanase polypeptide of claim 1, which is obtainable or originates from *Geomyces pannorum* strains RF 6293 having accession number CBS 119567 RF6546 having accession number CBS 119958 or RF6608 having accession number CBS 119962, or *Fusarium* cf *equiseti* strain RF6318 having accession number CBS 119568.

5. An isolated polynucleotide selected from the group consisting of:
   a) a nucleotide sequence having SEQ ID NO: 12, 14, 16, 18, 20 or 22,
   b) a complementary strand of a)
   c) a sequence that is degenerate as a result of the genetic code to any one of the sequences of a) or b).

6. The polynucleotide of claim 5, comprising a polynucleotide carried by *E. coli* DSM 18916, DSM 19171, DSM 19173, DSM 18915, DSM 18917, or DSM 19170.

7. An expression vector, comprising a polynucleotide of claim 5.

8. A host cell comprising the expression vector of claim 7.

9. Method for the production of an endoglucanase polypeptide of claim 1, comprising the steps of transforming a host cell with an expression vector encoding said polypeptide, and culturing said host cell under conditions enabling expression of said polypeptide, and optionally recovering and purifying said polypeptide.

10. An enzyme preparation comprising the endoglucanase polypeptide of claim 1.

11. A process for treating cellulosic material, wherein said process comprises contacting the cellulosic material with the endoglucanase polypeptide of claim 1, or enzyme preparation of claim 10.

12. The process of claim 11, which is carried out at a temperature of ≤50° C.

13. The process of claim 11, which is carried out at a pH of about 3-9.

14. The process of claim 11, which is biostoning or biofinishing.

15. The process of claim 11, which is hydrolysis of lignocellulosic material or a food application.

16. Detergent composition comprising the endoglucanase polypeptide of claim 1 or the enzyme preparation of claim 10.

17. Animal feed comprising the endoglucanase polypeptide of claim 1 or the enzyme preparation of claim 10.

18. *E. coli* strain having accession number DSM 18916, DSM 19171, DSM 19173, DSM 18915, DSM 18917, or DSM 19170.

19. The process of claim 11, which is carried out at a temperature of ≤40° C.

20. The process of claim 13, which is carried out at pH of about 4-8.

21. The process of claim 13, which is carried out at pH of 5-6.5.

* * * * *